US006982268B2

(12) United States Patent
Xie et al.

(10) Patent No.: US 6,982,268 B2
(45) Date of Patent: Jan. 3, 2006

(54) SUBSTITUTED IMIDAZOLYLMETHYL PYRIDINE AND PYRAZINE DERIVATIVES $GABA_A$ RECEPTOR LIGANDS

(75) Inventors: Linghong Xie, Guilford, CT (US); Manuka Ghosh, Brandford, CT (US); George Maynard, Clinton, CT (US)

(73) Assignee: Neurogen Corporation, Branford, CT (US)

( * ) Notice: Subject to any disclaimer, the term of this patent is extended or adjusted under 35 U.S.C. 154(b) by 114 days.

(21) Appl. No.: 10/431,257

(22) Filed: May 7, 2003

(65) Prior Publication Data

US 2003/0220348 A1   Nov. 27, 2003

Related U.S. Application Data

(60) Provisional application No. 60/379,117, filed on May 8, 2002.

(51) Int. Cl.
*A61K 31/4965* (2006.01)
*A61K 31/44* (2006.01)
*A01N 43/40* (2006.01)
*C07D 403/00* (2006.01)
*C07D 401/00* (2006.01)

(52) U.S. Cl. ................. 514/255.05; 514/333; 514/341; 544/295; 544/405; 546/256; 546/272.7

(58) Field of Classification Search ........... 514/255.05, 514/333, 341; 544/295, 405, 333; 546/256, 546/272.7
See application file for complete search history.

(56) References Cited

U.S. PATENT DOCUMENTS

| | | | |
|---|---|---|---|
| 5,017,591 A | 5/1991 | Matthews et al. | 514/369 |
| 5,147,863 A | 9/1992 | Matthews et al. | 514/63 |
| 6,127,395 A | 10/2000 | DeSimone et al. | 514/375 |
| 6,552,037 B2 | 4/2003 | Cai et al. | 514/303 |
| 2003/0069257 A1 | 4/2003 | Li et al. | 514/256 |

FOREIGN PATENT DOCUMENTS

| | | |
|---|---|---|
| DE | 26 51 580 | 6/1978 |
| GB | 2 054 567 | 2/1991 |
| WO | WO 01/12604 | 2/2001 |
| WO | WO 02/50062 | 6/2002 |
| WO | WO 03/033486 A1 | 4/2003 |

OTHER PUBLICATIONS

Hawley's Condensed Chemical Dictionary, 12th ed., Richard J. Lewis, Sr. , © 1993 by Van Nostrand Reinhold. p. 594.*
Concise Encyclopedia Chemistry, edited by Drs. Hans-Dieter Jakubke and Hans Jeschkeit, © 1993 by Walter de Gruyter & Co p. 490.*
McGraw-Hill Dictionary of Chemical Terms, 3rd ed. edited by Sybil P. Parker, © 1984 McGraw-Hill, Inc., p. 200.*
Murray, "Pyschosomatic Aspects of Gout" The Journal of General Psychology, vol. 103, pp. 131-138 (1980).*
Chesson et al, "Gout: nursing and medical actions" Nursing Standard, vol. 5(13,14), pp. 30-32 (Dec. 19, 1990).*
American Radiolabeled Chemicals catalog No. ARC-1127.
Cooper et al., (1991) *The Biochem. Basis of Neuropharm.* 6th Edition pp. 145-148.
Kuhnz (1998) *Drug Metabolism and Disposition* 26:1120-1127.
Mohler et al., (1995) *Neuroch. Res.* 20(5):631-636.
Oravcova, et al., (1996) *Journal of Chromatography B* 677:1-27.
White, et al. (1995) *Neuro Report* 6:1313-1316.
White, et al. (1995) *Receptor and Channels* 3:1-5.

* cited by examiner

*Primary Examiner*—James O. Wilson
*Assistant Examiner*—Zachary C. Tucker
(74) *Attorney, Agent, or Firm*—McDonnell Boehnen Hulbert & Berghoff LLP

(57) ABSTRACT

Substituted imidazolylmethyl pyridine and pyrazine derivatives that bind to $GABA_A$ receptors are provided. Such compounds may be used to modulate ligand binding to $GABA_A$ receptors in vivo or in vitro, and are particularly useful in the treatment of a variety of central nervous system (CNS) disorders in humans, domesticated companion animals and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting $GABA_A$ receptors (e.g., receptor localization studies).

20 Claims, No Drawings

SUBSTITUTED IMIDAZOLYLMETHYL PYRIDINE AND PYRAZINE DERIVATIVES GABA$_A$ RECEPTOR LIGANDS

CROSS-REFERENCE TO RELATED APPLICATIONS

This application claims priority from U.S. Provisional Application 60/379,117, filed May 8, 2002 which is incorporated herein by reference in its entirety.

FIELD OF THE INVENTION

This invention relates to substituted imidazolylmethyl pyridine and pyrazine derivatives. More specifically, it relates to such compounds that bind with high selectivity and/or high affinity to GABA$_A$ receptors. The invention also relates to pharmaceutical compositions comprising such compounds and to the use of such compounds in the treatment of central nervous system (CNS) diseases.

BACKGROUND OF THE INVENTION

The GABA$_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the GABA$_A$ receptor, which causes alteration in chloride conductance and membrane polarization. In addition to being the site of neurotransmitter action, a number of drugs including the anxiolytic and sedating benzodiazepines bind to this receptor. The GABA$_A$ receptor comprises a chloride channel that generally, but not invariably, opens in response to GABA, allowing chloride to enter the cell. This, in turn, effects a slowing of neuronal activity through hyperpolarization of the cell membrane potential.

GABA$_A$ receptors are composed of five protein subunits. A number of cDNAs for these GABA$_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native GABA$_A$ receptors are typically composed of 2α, 2β, and 1γ subunits (Pritchett & Seeburg (1989) Science 245:1389–1392, and Knight et al. (1998) Recept. Channels 6:1–18). Various lines of evidence (such as message distribution, genome localization and biochemical study results) suggest that the major naturally occurring receptor combinations are α$_1$β$_2$γ$_2$, α$_2$β$_3$γ$_2$, α$_3$β$_3$γ$_2$, and α$_5$β$_3$γ$_2$, (Mohler et al. (1995) Neuroch. Res. 20(5):631–36).

The GABA$_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the GABA$_A$ receptor. In addition to the benzodiazepine site (sometimes referred to as the benzodiazepine or BDZ receptor), the GABA$_A$ receptor contains sites of interaction for several other classes of drugs. These include a steroid binding site, a picrotoxin site, and a barbiturate site. The benzodiazepine site of the GABA$_A$ receptor is a distinct site on the receptor complex that does not overlap with the site of interaction for other classes of drugs that bind to the receptor or for GABA (see, e.g., Cooper, et al., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open GABA$_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as GABA$_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

GABA$_A$ selective ligands may also act to potentiate the effects of certain other CNS active compounds. For example, there is evidence that selective serotonin reuptake inhibitors (SSRIs) may show greater antidepressant activity when used in combination with GABA$_A$ selective ligands than when used alone.

SUMMARY OF THE INVENTION

The invention provides substituted imidazolylmethyl pyridine and pyrazine derivatives. The compounds of the invention bind to GABA$_A$ receptors, including human GABA$_A$ receptors and act as agonists, antagonists or inverse agonists of such receptors. These compounds are therefore useful in the treatment of a variety of CNS disorders. Preferred compounds bind with high selectivity and/or high affinity to GABA$_A$ receptors.

In a broad aspect, the invention provides compounds represented by Formula I, and pharmaceutically acceptable salts or prodrugs thereof.

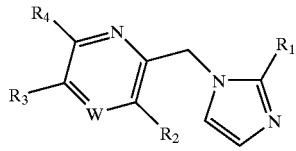

Formula I

Within Formula I:
W represents CH or N;
R$_1$ represents 5- to 10-membered aryl or heteroaryl, which is unsubstituted or substituted with from 1 to 4 groups independently selected from R$_5$;
R$_2$ represents hydrogen, halogen, C$_1$–C$_8$alkoxy, C$_1$–C$_8$alkyl, C$_2$–C$_8$alkenyl, C$_2$–C$_8$alkynyl, $C_3$-$C_{10}$cycloalkyl, $C_2$-$C_9$heterocycloalkyl, ($C_2$-$C_9$heterocycloalkyl)$C_1$-$C_8$alkyl or ($C_3$-$C_{10}$cycloalkyl)$C_1$-$C_8$alkyl, each of which is unsubstituted or substituted with from 1 to 3 substituents independently selected from $R_5$;

$R_3$ and $R_4$ are each independently selected from:
 (a) hydrogen, halogen, nitro and cyano; and
 (b) groups of the formula:

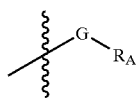

wherein: (i) G is a bond, $C_1$-$C_8$alkyl, —NH—, —N($R_B$)—, —($R_B$)N— —O—, —C(=O)—, —C(=O)NH—, —C(=O)N$R_B$—, —S(O)$_m$—, —CH$_2$C(=O)—, —S(O)$_m$NH—, —S(O)$_m$N$R_B$—, —NHC(=O)—, —C(=N$R_B$)—, HC=N—, —N$R_B$C(=O)—, —NHS(O)$_m$— or —N$R_B$S(O)—;
(ii) $R_A$ and $R_B$ are independently selected from $C_1$-$C_8$alkyl, $C_2$-$C_8$alkenyl, $C_2$-$C_8$alkynyl and 3- to 12-membered saturated, partially unsaturated and aromatic carbocycles and heterocycles having 1 ring or 2 fused, pendant or spiro rings, each of which is unsubstituted or substituted with from 1 to 4 substituents independently selected from $R_5$; and (iii) m is 0, 1 or 2; and $R_5$ is independently selected at each occurrence from halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$)alkoxy, oxo, amino($C_1$-$C_8$)alkyl and mono- and di($C_1$-$C_8$alkyl)amino($C_1$-$C_8$)alkyl.

The invention further provides pharmaceutical compositions comprising a compound as described above in combination with a physiologically acceptable carrier or excipient. Packaged pharmaceutical preparations are also provided, comprising such a pharmaceutical composition in a container and instructions for using the composition to treat a patient suffering from a CNS disorder such as anxiety, depression, a sleep disorder, attention deficit disorder or Alzheimer's dementia, or to improve short term memory.

Methods are provided, within further aspects, for the treatment of patients suffering from certain CNS disorders (such as anxiety, depression, a sleep disorder, attention deficit disorder or Alzheimer's dementia), comprising administering to a patient in need of such treatment a therapeutically effective amount of a compound as described above. The patient may be a human or other mammal. Treatment of humans, domesticated companion animals (pets) or livestock animals suffering from certain CNS disorders with an effective amount of a compound of the invention is encompassed by the present invention.

Methods are also provided for enhancing short term memory in a patient, comprising administering to a patient in need of such treatment a therapeutically effective amount of a compound as described above. The patient may be a human or other mammal.

Within other aspects, the present invention provides methods for potentiating a therapeutic effect of a CNS agent, comprising administering to a patient a CNS agent and a compound as described above.

Methods for determining the presence or absence of GABA$_A$ receptor in a sample (e.g., a tissue section) are further provided, comprising the steps of: (a) contacting a sample with a compound as described above under conditions that permit binding of the compound to GABA$_A$ receptor; and (b) detecting a level of compound bound to GABA$_A$ receptor.

The invention further provides, within other aspects, methods for altering the signal-transducing activity of GABA$_A$ receptor, comprising contacting a cell expressing GABA$_A$ receptor with a compound as described above in an amount sufficient to detectably alter the electrophysiology of the cell.

These and other aspects of the invention will become apparent upon reference to the following detailed description.

DETAILED DESCRIPTION OF THE INVENTION

As noted above, the invention provides 2-imidazol-1-ylmethyl-pyridine and 2-imidazole-1-ylmethyl-pyrazine derivatives that bind (preferably with high affinity and/or high selectivity) to GABA$_A$ receptor, including human GABA$_A$ receptor. Without wishing to be bound to any particular theory, it is believed that the interaction of the compounds provided herein with the benzodiazepine site results in the biological activity of these compounds. Compounds provided herein may be used in a variety of in vivo and in vitro contexts, as discussed in further detail below.

Definitions

Compounds of the invention are generally described using standard nomenclature. Reference to a compound structure generally encompasses addition salts, hydrates and acylated prodrugs of the indicated structure. The compounds herein described may have one or more asymmetric centers or planes. Many geometric isomers of olefins, C=N double bonds, and the like can also be present in the compounds described herein, and all such stable isomers are contemplated in the invention. Cis and trans geometric isomers of the compounds of the invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Certain compounds are described herein using a general formula that includes variables. Unless otherwise specified, each variable within such a formula is defined independently of all other variables, and any variable that occurs more than one time within a formula is defined independently at each occurrence. Thus, for example, if a group is described as being substituted with 0–2 R*, then the group may be unsubstituted or substituted with up to two R* groups and the definition of any one R* is independent from the definition of any other R*. In addition, it will be apparent that combinations of substituents and/or variables are permissible only if such combinations result in stable compounds.

When any group, such as an aryl group, heteroaryl group, carbocycle or heterocycle, is said to be "substituted by one or more substituents" that group may contain from 1 to the maximum number of substituents allowable without exceeding the valency of the atoms of the substituted group. Preferably, such groups are substituted with from 1 to 4 substituents; more preferably, such groups are substituted with from 1 to 3 substituents. Such groups are further preferably substituted with zero or one oxo substituent. An "optionally substituted" group may be unsubstituted or substituted with from 1 to the maximum number of substituents indicated.

As used herein, "alkyl" refers to branched and straight-chain hydrocarbon groups. Preferred alkyl groups are $C_1$–$C_8$alkyl (i.e., alkyl groups having from 1 to 8 carbon atoms), with $C_1$–$C_6$alkyl and $C_1$–$C_4$alkyl particularly preferred. Examples of alkyl groups include, but are not limited to, methyl, ethyl, n-propyl, i-propyl, n-butyl, s-butyl, t-butyl, n-pentyl, isopentyl, s-pentyl, hexyl, 2-hexyl, 3-hexyl and 5-methylpentyl. An alkyl group may be bonded to an atom within a molecule of interest via any chemically suitable portion of the alkyl group.

The term "cycloalkyl" is intended to include saturated ring groups, having the specified number of carbon atoms, such as cyclopropyl, cyclobutyl, cyclopentyl, cyclohexyl or cycloheptyl. $C_3$–$C_{10}$cycloalkyl groups have from 3 to 10 ring members; preferred cycloalkyl groups have 4 to 8 and more preferably 5 to 7 ring members.

"Heterocycloalkyl" refers to saturated ring groups that comprise at least one heteroatom (i.e., N, S or O), with the remainder of the ring members carbon. Heterocycloalkyl groups typically include 3 to 10 rings members, preferably 4 to 8 and more preferably 5 to 7 ring members. Heterocycloalkyl groups typically have from 1 to 3 heteroatoms; preferably not more than one S or O atom is present in a heterocycloalkyl group. Preferred heterocycloalkyl groups include morpholinyl, piperidinyl, piperazinyl, thiomorpholinyl, and pyrrolidinyl.

In the term "(cycloalkyl)alkyl" or ($C_3$–$C_{10}$cycloalkyl) $C_1$–$C_8$alkyl, cycloalkyl and alkyl are as defined above and the point of attachment is on the alkyl group. This term encompasses, but is not limited to, cyclopropylmethyl, cyclobutylmethyl, cyclopentylmethyl, cyclohexylmethyl and cycloheptylmethyl. "(Heterocycloalkyl)alkyl" refers to such groups that comprise at least one heteroatom within the ring, as described above.

As used herein, "alkoxy" represents an alkyl group as defined above attached via an oxygen bridge. Preferred alkoxy groups have from 1 to 8 carbon atoms (i.e., $C_1$–$C_8$alkoxy). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, iso-pentoxy, neopentoxy, n-hexoxy, 2-hexoxy, 3-hexoxy and 3-methylpentoxy. "$C_1$–$C_6$alkoxy" (alkoxy groups having from 1 to 6 carbon atoms) are preferred, with $C_1$–$C_4$alkoxy particularly preferred.

"Alkenyl" is intended to include hydrocarbon chains of either a straight or branched configuration comprising one or more unsaturated carbon-carbon bonds which may occur in any stable point along the chain, such as ethenyl and propenyl. Alkenyl groups typically will have 2 to about 8 carbon atoms, more typically 2 to about 6 carbon atoms. A "stable point" is bond that, when unsaturated, results in a chemically stable compound (i.e., a compound that can be isolated, characterized and tested for biological activity).

"Alkynyl" is intended to include hydrocarbon chains of either a straight or branched configuration comprising one or more triple carbon-carbon bonds which may occur in any stable point along the chain, such as ethynyl and propynyl. Alkynyl groups typically will have 2 to about 8 carbon atoms, more typically 2 to about 6 carbon atoms.

A "carbocycle" is a group that comprises at least one ring formed entirely by carbon-carbon bonds (referred to herein as a carbocyclic ring). Unless otherwise specified, such a ring may be aromatic or non-aromatic. A carbocycle generally has from 1 to 3 fused or pendant carbocyclic rings, preferably one ring or two fused carbocyclic rings. Typically, each ring contains from 3 to 8 (preferably from 5 to 7) ring members; carbocycles comprising fused or pendant ring systems typically contain from 9 to 12 ring members. Certain carbocycles are saturated cycloalkyl groups, as described above. Other carbocycles are "partially saturated" (i.e., comprise one or more double or triple bonds within a ring, but are not aromatic) or aryl groups (i.e., aromatic groups having 1 or more rings, wherein all members of the aromatic ring or rings are carbon). Preferred aryl groups include 5- to 10-membered groups (i.e., single 5- to 7-membered rings or 7- to 10-membered bicyclic groups), such as phenyl and naphthyl. "Arylalkyl" groups (wherein aryl and alkyl are as defined above and the point of attachment is on the alkyl group) are also encompassed by the term "carbocycle." Such groups include, but are not limited to, benzyl. Carbon atoms present within a carbocycle ring may, of course, be further bonded to a variety of ring substituents, such as (but not limited to) hydrogen, a halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl) alkyl, ($C_3$–$C_{10}$cycloalkyl)alkoxy, $C_2$–$C_9$heterocycloalkyl, $C_1$–$C_8$alkenyl, $C_1$–$C_8$alkynyl, halo ($C_1$–$C_8$)alkyl, halo($C_1$–$C_8$)alkoxy, oxo, amino($C_1$–$C_8$)alkyl and mono- and di($C_1$–$C_8$alkyl)amino($C_1$–$C_8$)alkyl.

A "heterocycle" is a group that comprises at least one ring in which at least one ring atom is a heteroatom (i.e., N, O or S), and the remainder of the ring atoms are carbon. Such a ring is referred to as a heterocyclic ring. Preferably, a heterocyclic ring comprises 1–4 heteroatoms; within certain embodiments 1 or 2 heteroatoms is preferred. A heterocycle generally has from 1 to 3 fused or pendant rings (at least one of which is heterocyclic), preferably one ring or two fused rings. Typically, each ring contains from 3 to 8 ring members (preferably from 5 to 7 ring members); heterocycles comprising fused or pendant rings typically contain from 9 to 12 ring members. 3- to 10-membered heterocyclic groups that contain 1 heterocyclic ring or 2 fused rings (at least one of which is heterocyclic; for a total of 3 to 10 ring members) are preferred, with 5- to 10-membered heterocyclic groups particularly preferred. Heterocycles may be optionally substituted with one or more substituents as described above for carbocycles. Unless otherwise specified, a heterocycle may be saturated (i.e., heterocycloalkyl, as described above), partially saturated or aromatic (heteroaryl). As used herein the term "heteroaryl", is intended to mean stable 5-to 7-membered monocyclic and 7-to 10-membered bicyclic heterocyclic aromatic rings which consist of carbon atoms and from 1 to 4 heteroatoms independently selected from the group consisting of N, O and S. It is preferred that the total number of S and O atoms in the heteroaryl group, i.e., in the ring system, is not more than 1. In the term "heteroarylalkyl," heteroaryl and alkyl are as defined above and the point of attachment to the parent system is on the alkyl group.

Examples of heteroaryl groups include, but are not limited to, pyrimidinyl, pyridyl, quinolinyl, benzothienyl, indolyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydro-benzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide and benzothiopyranyl S,S-dioxide. Preferred heteroaryl groups include imidazolyl, pyrrolyl, pyridyl, thiazolyl, pyrazolyl, thiazolyl, isoxazolyl, triazolyl, tetrazolyl, oxadiazolyl, pyrimidinyl and oxazolyl, with pyridyl particularly preferred.

The term "halogen" includes fluorine, chlorine, bromine and iodine.

As used herein, "haloalkyl" refers to alkyl groups that are substituted with 1 or more halogen (for example —$C_vF_w$ where v is an integer of from 1 to 3 and w is an integer of from 1 to (2 v+1). Examples of haloalkyl groups include, but are not limited to, mono-, di- and tri-fluoromethyl; mono-, di- and tri-chloromethyl; mono-, di-, tri-, tetra- and penta-fluoroethyl; and mono-, di-, tri-, tetra- and penta-chloroethyl. "Halo($C_1$–$C_8$)alkyl", groups have 1 to 8 carbon atoms.

The term "haloalkoxy" refers to a haloalkyl group as defined above attached via an oxygen bridge. "Halo($C_1$–$C_8$) alkoxy" groups have 1 to 8 carbon atoms. Examples of haloalkoxy groups include, but are not limited to, mono-, di- and tri-fluoromethoxy.

The term "oxo," as used herein, refers to a keto (C=O) group. An oxo group that is a substituent of a nonaromatic ring results in a conversion of —$CH_2$— to —C(=O)—. It will be apparent that the introduction of an oxo substituent on an aromatic ring destroys the aromaticity.

A "substituent," as used herein, refers to a molecular moiety that is covalently bonded to an atom within a molecule of interest. For example, a "ring substituent" may be a moiety such as a halogen, alkyl group, alkoxy group, haloalkyl group or other group as discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution. Representative substituents include, but are not limited to, halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl)alkyl, ($C_3$–$C_{10}$cycloalkyl)alkoxy, $C_2$–$C_9$heterocycloalkyl, $C_1$–$C_8$alkenyl, $C_1$–$C_8$alkynyl, halo ($C_1$–$C_8$)alkyl, halo($C_1$–$C_8$)alkoxy, oxo, amino($C_1$–$C_8$)alkyl and mono- and di($C_1$–$C_8$alkyl) amino ($C_1$–$C_8$) alkyl.

A dash ("-") that is not between two letters or symbols is used to indicate a point of attachment for a substituent. For example, —$CONH_2$ is attached through the carbon atom.

The term "$GABA_A$ receptor" refers to a protein complex that detectably binds GABA and mediates a dose dependent alteration in chloride conductance and membrane polarization. Receptors comprising naturally-occurring mammalian (especially human or rat) $GABA_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate $GABA_A$ receptor for GABA may be evaluated using a standard ligand binding assay as provided herein. It will be apparent that there are a variety of $GABA_A$ receptor subtypes that fall within the scope of the term "$GABA_A$ receptor." These subtypes include, but are not limited to, $\alpha_2\beta_3\gamma_2$, $\alpha_3\beta_3\gamma_2$, $\alpha_5\beta_3\gamma_2$, and $\alpha_1\beta_2\gamma_2$ receptor subtypes. $GABA_A$ receptors may be obtained from a variety of sources, such as from preparations of rat cortex or from cells expressing cloned human $GABA_A$ receptors. Particular subtypes may be readily prepared using standard techniques (e.g., by introducing mRNA encoded the desired subunits into a host cell, as described herein).

A "prodrug" is a compound that may not fully satisfy the structural requirements of the compounds provided herein, but is modified in vivo, following administration to a patient, to produce an active compound of the present invention. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino or sulfhydryl group, respectively. Examples of prodrugs include, but are not limited to, acetate, formate and benzoate derivatives of alcohol and amine functional groups within the compounds provided herein.

A "patient" is any individual treated with a compound provided herein. Patients include humans, as well as other animals such as companion animals and livestock. Patients may be afflicted with a CNS disorder, or may be free of such a condition (i.e., treatment may be prophylactic).

A "CNS disorder" is a disease or condition of the central nervous system that is responsive to $GABA_A$ receptor modulation in the patient. Such disorders include anxiety disorders (e.g., panic disorder, obsessive compulsive disorder, agoraphobia, social phobia, specific phobia, dysthymia, adjustment disorders, separation anxiety, cyclothymia, and generalized anxiety disorder), stress disorders (e.g., post-traumatic stress disorder, anticipatory anxiety acute stress disorder and acute stress disorder), depressive disorders (e.g., depression, a typical depression, bipolar disorder and depressed phase of bipolar disorder), sleep disorders (e.g., primary insomnia, circadian rhythm sleep disorder, dyssomnia NOS, parasomnias including nightmare disorder, sleep terror disorder, sleep disorders secondary to depression, anxiety and/or other mental disorders and substance-induced sleep disorder), cognitive disorders (e.g., cognition impairment, mild cognitive impairment (MCI), age-related cognitive decline (ARCD), traumatic brain injury, Down's Syndrome, neurodegenerative diseases such as Alzheimer's disease and Parkinson's disease, and stroke), AIDS-associated dementia, dementia associated with depression, anxiety or psychosis, attention deficit disorders (e.g., attention deficit disorder and attention deficit and hyperactivity disorder), convulsive disorders (e.g., epilepsy), benzodiazepine overdose and drug and alcohol addiction.

A "CNS agent" is any drug used to treat or prevent a CNS disorder. CNS agents include, for example: serotonin receptor (e.g., 5-$HT_{1A}$) agonists and antagonists and selective serotonin reuptake inhibitors (SSRIs); neurokinin receptor antagonists; corticotropin releasing factor receptor ($CRF_1$) antagonists; melatonin receptor agonists; nicotinic agonists; muscarinic agents; acetylcholinesterase inhibitors and dopamine receptor agonists.

A compound is said to have "high affinity" if the $K_i$ at a $GABA_A$ receptor is less than 1 micromolar, preferably less than 100 nanomolar or less than 10 nanomolar. A representative assay for determining $K_i$ at $GABA_A$ receptor is provided in Example 3, herein. It will be apparent that the $K_i$ may depend upon the receptor subtype used in the assay. In other words, a high affinity compound may be "subtype-specific" (i.e., the $K_i$ is at least 10-fold greater for one subtype than for another subtype). Such compounds are said to have high affinity for $GABA_A$ receptor if the $K_i$ for at least one $GABA_A$ receptor subtype meets the above criteria.

A compound is said to have "high selectivity" if it binds to a $GABA_A$ receptor with a $K_i$ that is at least 10-fold lower, preferably at least 100-fold lower, than the $K_i$ for binding to other membrane-bound receptors. In particular, the compound should have a $K_i$ that is at least 10-fold greater at the following receptors than at a $GABA_A$ receptor: serotonin, dopamine, galanin, VR1, C5a, MCH, NPY, CRF, bradykinin, NK-1, NK-3 and tackykinin. Assays to determine the $K_i$ at other receptors may be performed using standard binding assay protocols.

Preferred compounds of Formula I are those in which $R_1$ is a 5- or 6-membered aromatic ring, unsubstituted or substituted with from 1 to 4 groups independently selected from $R_5$. Representative preferred $R_1$ groups include phenyl, pyridyl, pyrimidyl and thiazolyl, unsubstituted or substituted with from 1 to 3 groups independently selected from halogen, cyano, $C_1$–$C_6$alkyl, halo($C_1$–$C_6$)alkyl, $C_1$–$C_6$alkoxy and halo($C_1$–$C_6$)alkoxy. Preferred $R_1$ substituents include halogen, OH, $C_1$–$C_6$alkyl, and $CF_3$. $R_1$ may be, for example, substituted with one or two halogens, such as fluorine.

Preferred compounds include those of Formula II, wherein A and B are each independently CH or N, and other variable positions are as defined above:

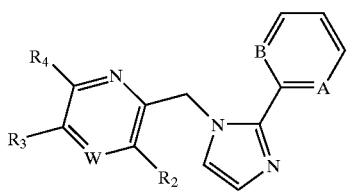

Formula II $R_2$ in Formula I and II is preferably halogen, $C_1$–$C_6$alkoxy, $C_1$–$C_6$alkyl or $C_2$–$C_9$heterocycloalkyl$C_1$–$C_8$alkyl, more preferably $C_1$–$C_4$alkoxy or halogen, or a 5- or 6-membered aryl or heteroaryl.

$R_3$ and $R_4$ of Formulas I and II are preferably independently selected from hydrogen, halogen, alkyl, alkoxy, haloalkyl, and 5- to 7-membered aromatic carbocycles and heterocycles, wherein the carbocycles and heterocycles are unsubstituted or substituted with halogen, trifluoromethyl or methyl. More preferably, $R_3$ and $R_4$ are independently hydrogen, $C_1$–$C_4$alkoxy or 5- to 7-membered aromatic carbocycle wherein carbocycle is unsubstituted or substituted with halogen, trifluoromethyl or methyl. Still more preferably, $R_3$ and $R_4$ are independently hydrogen, $C_1$–$C_4$alkoxy or phenyl, wherein the phenyl is unsubstituted or substituted with halogen, trifluoromethyl or methyl.

Preferred compounds of formula I and II also include compounds wherein $R_3$ is phenyl unsubstituted or substituted with halogen, trifluoromethyl or methyl, and $R_4$ is hydrogen.

Preferred compounds of formula I and II also include compounds wherein $R_3$ is $C_1$–$C_4$alkoxy, and $R_4$ is hydrogen.

Preferred compounds of formula I and II also include compounds wherein $R_4$ is phenyl unsubstituted or substituted with halogen, trifluoromethyl or methyl, and $R_3$ is hydrogen.

Preferred compounds of formula I and II also include compounds wherein $R_4$ is $C_1$–$C_4$alkoxy, and $R_3$ is hydrogen.

Representative compounds of the invention include the folowing:

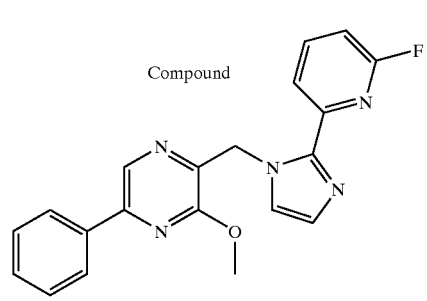

Compound

Cmpd. No. 1

2-[2-(6-fluoro-pyridin-2-yl)-imidazol-1-ylmethyl]-3-methoxy-5-phenyl-pyrazine

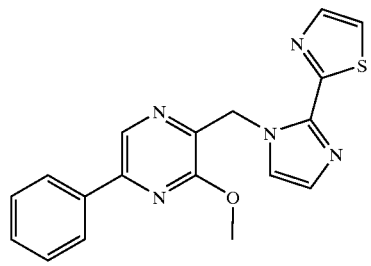

3-methoxy-5-phenyl-2-(2-thiazol-2-yl-imidazol-1-ylmethyl)-pyrazine

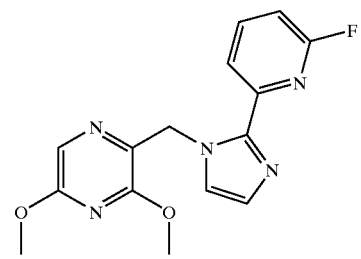

2-[2-(6-fluoro-pyridin-2-yl)-imidazol-1-ylmethyl] -3,5-dimethoxy-pyrazine

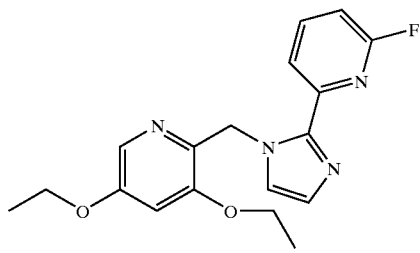

2-[2-(6-fluoro-pyridin-2-yl)-imidazol-1-ylmethyl]-3,5-diethoxy-pyridine

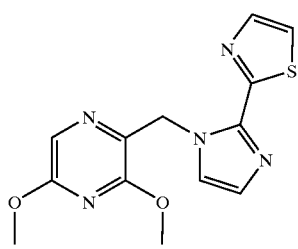

3,5-dimethoxy-2-(2-thiazol-2-yl-imidazol-1-ylmethyl)-pyrazine

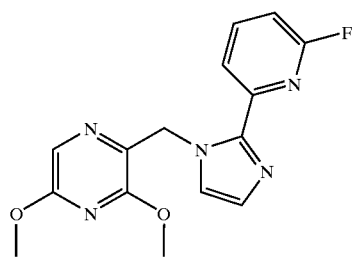

3-chloro-2-[2-(6-fluoro-pyridin-2-yl)-imidazol-1-ylmethyl]-5-methoxy-pyrazine

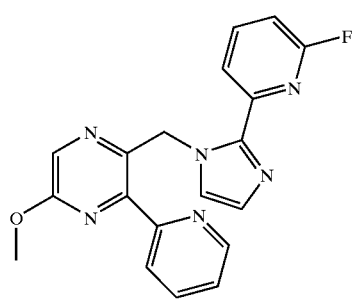

2-[2-(6-fluoro-pyridin-2-yl)-imidazol-1-ylmethyl]-5-methoxy-3-pyridin-2-yl-pyrazine

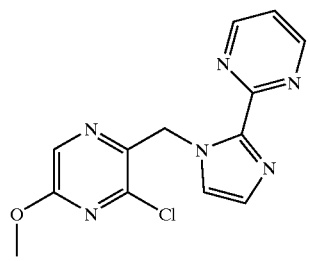

2-[1-(3,5-dimethoxy-pyrazin-2-ylmethyl)1H-imidazol-2-yl]-pyrimidine

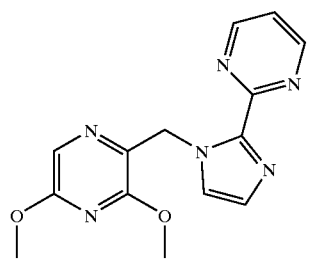

2-[1-(3,5-dimethoxy-pyrazin-2-ylmethyl)-1H-imidazol-2-yl]-pyrimdine

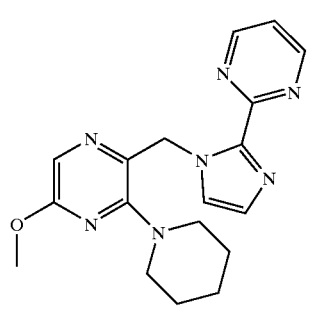

2-[1-(5-methoxy-3-piperidin-1-yl-pyrazin-2-ylmethyl)-1H-imidazol-2-yl]-pyrimidine It will be apparent that the specific compounds recited above are illustrative examples of compounds provided herein, and are not intended to limit the scope of the present invention. As noted above, all compounds of the present invention may be present as a free base or as a physiologically acceptable acid addition salt. In addition, both chiral compounds and racemic mixtures are encompassed by the present invention.

Compounds provided herein detectably alter (modulate) ligand binding to $GABA_A$ receptor, as determined using a standard in vitro receptor binding assay. References herein to a "$GABA_A$ receptor ligand binding assay" are intended to refer to the standard in vitro receptor binding assay provided in Example 3. Briefly, a competition assay may be performed in which a $GABA_A$ receptor preparation is incubated with labeled (e.g., $^3H$) ligand, such as Flumazenil, and unlabeled test compound. Incubation with a compound that detectably modulates ligand binding to $GABA_A$ receptor will result in a decrease or increase in the amount of label bound to the $GABA_A$ receptor preparation, relative to the amount of label bound in the absence of the compound. Preferably, such a compound will exhibit a $K_i$ at $GABA_A$ receptor of less than 1 micromolar, more preferably less than 500 nM, 100 nM, 20 nM or 10 nM. The $GABA_A$ receptor used to determine in vitro binding may be obtained from a variety of sources, for example from preparations of rat cortex or from cells expressing cloned human $GABA_A$ receptors.

If desired, compounds provided herein may be evaluated for certain pharmacological properties including, but not limited to, solubility, oral bioavailability, toxicity, serum protein binding, lack of clinically relevant EKG effect and in vitro and in vivo half-life. Routine assays that are well known in the art may be used to assess these properties, and identify superior compounds for a particular use. For example, solubility in aqueous solutions is preferably at least 500 ng/mL. Assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1–27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120–27.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). Toxicity may be also evaluated using the assay detecting an effect on cellular ATP production provided in Example 5, or toxicity to cultured hepatocytes. Other assays that may be used include bacterial reverse mutation assays, such as an Ames test, as well as standard teratogenicity and tumorogenicity assays. Preferably, administration of compounds provided herein at certain doses (i.e., doses yielding effective in vivo concentrations) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75%, and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

For detection purposes, as discussed in more detail below, compounds provided herein may be isotopically-labeled or radiolabeled. Such compounds are identical to those described above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Compounds

Compounds provided herein may generally be prepared using standard synthetic methods. Starting materials are generally readily available from commercial sources, such as Sigma-Aldrich Corp. (St. Louis, Mo.), or may be prepared as described herein. Representative procedures suitable for the preparation of compounds of Formula I are outlined in Schemes I and II, which are not to be constructed as limiting the invention in scope or spirit to the specific reagents and conditions shown in them. Those having skill in the art will recognize that the reagents and conditions may be varied and additional steps employed to produce compounds encompassed by the present invention. In some cases, protection of reactive functionalities may be necessary to achieve the desired transformations. In general, such need for protecting groups, as well as the conditions necessary to attach and remove such groups, will be apparent to those skilled in the art of organic synthesis. Unless otherwise stated in the schemes below, the variables are as defined in Formula I.

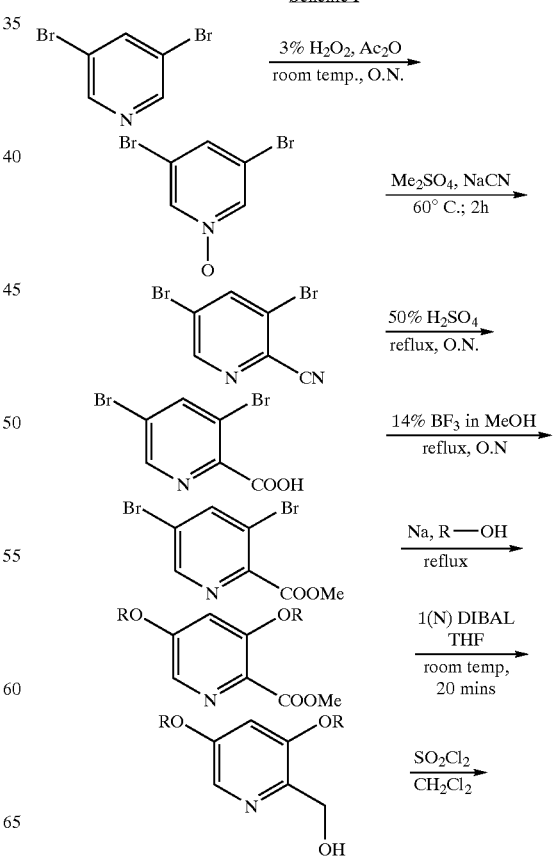

Scheme I

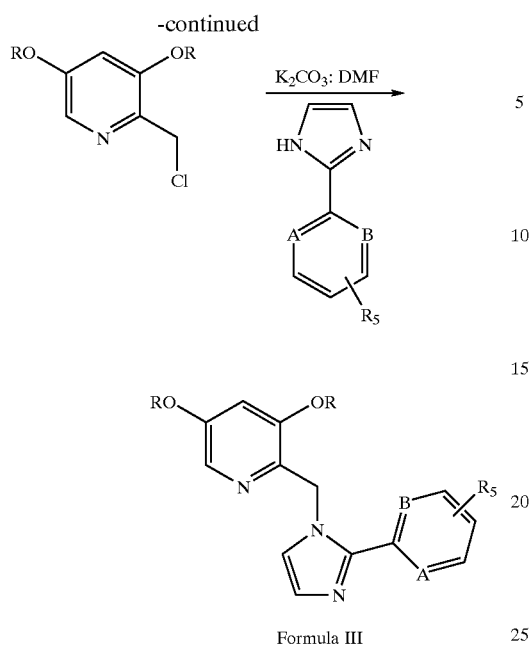

Formula III

Scheme I illustrates the synthesis of certain representative imidazolylmethyl pyridines. Briefly, 3,5-dibromo-pyridine-2-carboxylic acid methyl ester is added to a stirred solution of sodium in an alcohol and refluxed to yield the alkoxy-substituted derivative. Reaction with diisobutylaluminum hydride (DIBAL), followed by thionyl chloride, results in the chloromethyl-substituted pyridine, which is then reacted with an imidazolyl aryl or heteroaryl to yield a compound of Formula III. It will be readily apparent that 3,5-dibromo-2-cyanopyridine may be subjected to other straightforward synthetic transformations to introduce additional $R_2$ and $R_3$ substituents encompassed by Formula I.

Scheme II

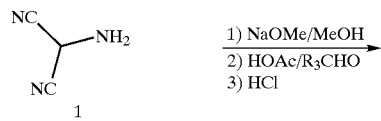

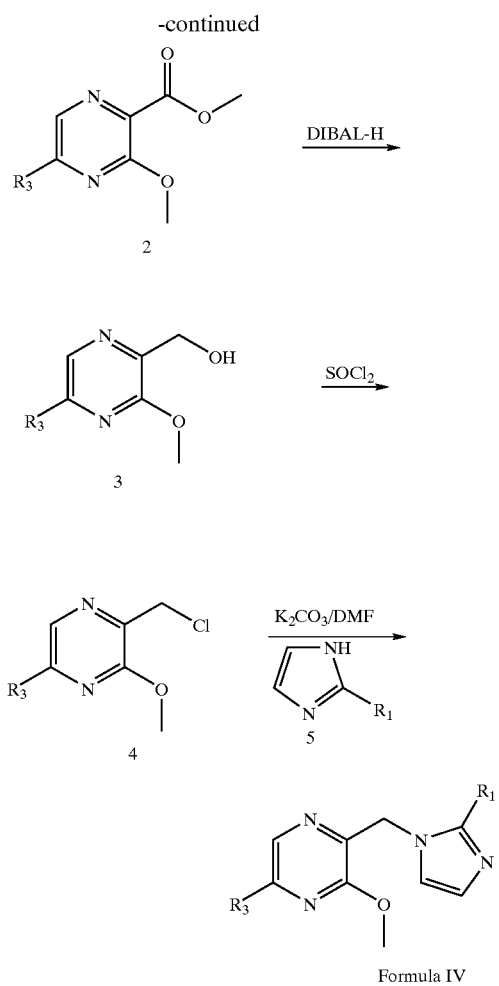

Formula IV

Scheme II illustrates the synthesis of certain representative imidazolylmethyl pyrazines. Briefly, 2-amino-malonitrile 4-toluene sulfonate is reacted with NaOMe, followed by an aldehyde and HCl to yield the pyrazine 2-carboxylic acid 2. Reaction with DIBAL, followed by SOCl$_2$, results in the 2-chloromethyl pyrazine 4. Compounds of Formula IV are then generated by reaction with the substituted imidazole 5.

Scheme III

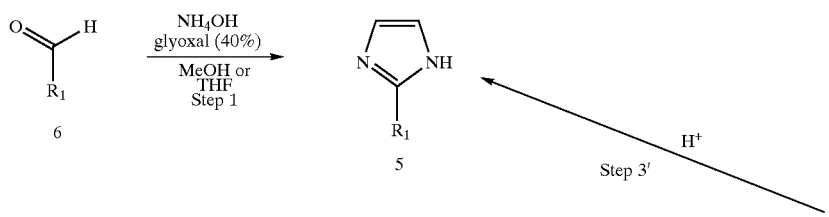

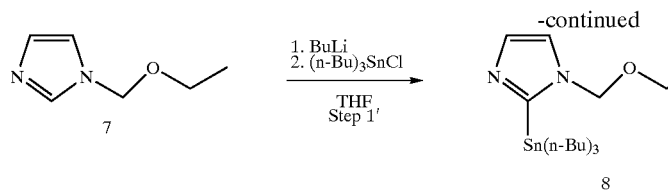 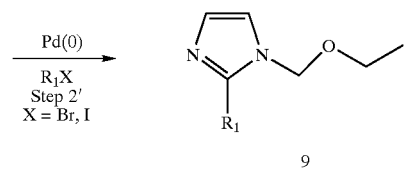

Scheme III illustrates two routes for the synthesis of imidazole intermediate 5 used within Scheme II. In Step 1, an aryl or heteroaryl aldehyde 6 is treated with glyoxal and ammonium hydroxide to form the imidazole intermediate 5. In Step 1', imidazole 7 is treated with butyl lithium followed by tri-n-butyltin chloride to obtain compound 8, which must be handled with care to avoid decomposition. In Step 2', compound 8 is utilized in a palladium cross-coupling reaction with an aryl or heteroaryl halide to obtain compound 9. Subsequent treatment of 9 with acid in Step 3' provides compound 5.

It will be apparent that the starting materials may be varied and additional steps employed to produce the varied compounds encompassed by the present invention.

In certain situations, compounds provided herein may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished by conventional methods, such as crystallization in the presence of a resolving agent, or chromatography using, for example, a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication, commensurate with a reasonable benefit/risk ratio. Those skilled in the art will recognize a wide variety of non-toxic pharmaceutically acceptable addition salts, including mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfinic, sulfanilic, formic, toluenesulfonic, methanesulfonic, ethane disulfonic, 2-hydroxyethylsulfonic, oxalic, isethionic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Compounds may be radiolabeled by carrying out their synthesis using precursors comprising at least one atom that is a radioisotope. Such radioisotope(s) are preferably selected from carbon (preferably $^{14}C$), hydrogen (preferably $^{3}H$), sulfur (preferably $^{35}S$), or iodine (preferably $^{125}I$). Synthesis of such radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed above using the compound as substrate. In addition, certain precursors may be subjected to tritium-halogen exchange with tritium gas, tritium gas reduction of unsaturated bonds, or reduction using sodium borotritide, as appropriate. $^{14}C$ radiolabeled compounds of the invention may be prepared using $^{14}C$ radiolabeled diethyl oxalate (AMERICAN RADIOLA- BELED CHEMICALS, St. Louis, Mo., catalog no. ARC-1127) as a starting material for the synthesis outlined in Scheme I.

Pharmaceutical Compositions

The present invention also provides pharmaceutical compositions comprising at least one compound provided herein, together with at least one physiologically acceptable carrier or excipient. Such compounds may be used for treating disorders responsive to $GABA_A$ receptor modulation (e.g., treatment of anxiety, depression, sleep disorders or cognitive impairment by $GABA_A$ receptor modulation). Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs). If desired, other active ingredients may also be included, such as CNS agents.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with one or more excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectible aqueous or oleaginous suspension. The compound, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of active compound release. The amount of compound contained within a sustained release formulation depends upon the site of implantation, the rate and expected duration of release and the nature of the condition to be treated or prevented.

Compounds provided herein are generally present within a pharmaceutical composition in a therapeutically effective amount. A therapeutically effective amount is an amount that results in a discernible patient benefit, such as diminution of symptoms of a CNS disorder. A preferred concentration is one sufficient to inhibit the binding of $GABA_A$ receptor ligand to $GABA_A$ receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating a CNS disorder such as anxiety, depression, a sleep disorder, attention deficit disorder or Alzheimer's dementia. Packaged pharmaceutical preparations include a container holding a therapeutically effective amount of at least one compound as described herein and instructions (e.g., labeling) indicating that the contained composition is to be used for treating the CNS disorder.

Methods of Use

Within certain aspects, the present invention provides methods for inhibiting the development of a CNS disorder. In other words, therapeutic methods provided herein may be used to treat a disorder, or may be used to prevent or delay the onset of such a disease in a patient who is free of detectable CNS disorder. CNS disorders are discussed in more detail below, and may be diagnosed and monitored using criteria that have been established in the art. Alternatively, or in addition, compounds provided herein may be administered to a patient to improve short-term memory. Patients may include humans, domesticated companion animals (pets, such as dogs) and livestock animals, with dosages and treatment regimes as described above.

Frequency of dosage may vary, depending on the compound used and the particular disease to be treated or prevented. In general, for treatment of most disorders, a dosage regimen of 4 times daily or less is preferred. For the treatment of sleep disorders a single dose that rapidly reaches effective concentrations is desirable. Patients may generally be monitored for therapeutic effectiveness using assays suitable for the condition being treated or prevented, which will be familiar to those of ordinary skill in the art.

Within certain embodiments, compounds provided herein are used to treat patients in need of such treatment, in an amount sufficient to alter the symptoms of a CNS disorder. Compounds that act as agonists at $\alpha_2\beta_3\gamma_2$ and $\alpha_3\beta_3\gamma_2$ receptor subtypes are particularly useful in treating anxiety disorders such as panic disorder, obsessive compulsive disorder and generalized anxiety disorder; stress disorders including post-traumatic stress, and acute stress disorders. Compounds that act as agonists at $\alpha_2\beta_3\gamma_2$ and $\alpha_3\beta_3\gamma_2$ receptor subtypes are also useful in treating depressive or bipolar disorders and in treating sleep disorders. Compounds that act as inverse agonists at the $\alpha_5\beta_3\gamma_2$ receptor subtype or $\alpha_1\beta_2\gamma_2$ and $\alpha_5\beta_3\gamma_2$ receptor subtypes are particularly useful in treating cognitive disorders including those resulting from Down's Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

CNS disorders that can be treated using compounds and compositions provided herein include:

Depression, e.g., depression, a typical depression, bipolar disorder, depressed phase of bipolar disorder.

Anxiety, e.g., general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g., sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g., cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety and psychosis (including schizophrenia and hallucinatory disorders).

Attention Deficit Disorder, e.g., attention deficit disorder (ADD), and attention deficit and hyperactivity disorder (ADHD).

Speech disorders, e.g., motor tic, clonic stuttering, dysfluency, speech blockage, dysarthria, Tourette's syndrome and logospasm.

Compounds and compositions provided herein can also be used to improve short-term memory (working memory) in a patient. A therapeutically effective amount of a compound for improving short-term memory loss is an amount sufficient to result in a statistically significant improvement in any standard test of short-term memory function, including forward digit span and serial rote learning. For example, such a test may be designed to evaluate the ability of a patient to recall words or letters. Alternatively, a more complete neurophysical evaluation may be used to assess short-term memory function. Patients treated in order to improve short-term memory may, but need not, have been diagnosed with memory impairment or considered predisposed to development of such impairment.

In a separate aspect, the present invention provides methods for potentiating the action (or therapeutic effect) of other CNS agent(s). Such methods comprise administering an effective amount of a compound provided herein in combination with another CNS agent. CNS agents include, but are not limited to the following: for anxiety, serotonin receptor (e.g., 5-HT$_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Within certain embodiments, the present invention provides a method of potentiating the antidepressant activity of selective serotonin reuptake inhibitors (SSRIs) by administering an effective amount of a GABA agonist compound of the invention in combination with an SSRI. An effective amount of compound is an amount sufficient to result in a detectable change in patient symptoms, when compared to a patient treated with the other CNS agent alone.

Combination administration can be carried out in a fashion analogous to that disclosed in Da-Rocha, et al., *J. Psychopharmacology* (1997) 11(3):211–218; Smith, et al., *Am. J. Psychiatry* (1998) 155(10):1339–45; or Le, et al., *Alcohol and Alcoholism* (1996) 31(suppl.):127–132. See also PCT International Publication Nos. WO 99/47142; WO 99/47171; WO 99/47131; and WO 99/37303.

The present invention also pertains to methods of inhibiting the binding of benzodiazepine compounds, such as Ro15-1788 or GABA, to the GABA$_A$ receptors. Such methods involve contacting a compound provided herein with cells expressing GABA$_A$ receptor, wherein the compound is present in an amount sufficient to inhibit benzodiazepine binding or GABA binding to GABA$_A$ receptors in vitro. This method includes inhibiting the binding of benzodiazepine compounds to GABA$_A$ receptors in vivo (e.g., in a patient given an amount of a compound provided herein that would be sufficient to inhibit the binding of benzodiazepine compounds or GABA to GABA$_A$ receptors in vitro). In one embodiment, such methods are useful in treating benzodiazepine drug overdose. The amount of a compound that would be sufficient to inhibit the binding of a benzodiazepine compound to the GABA$_A$ receptor may be readily determined via an GABA$_A$ receptor binding assay, such as the assay described in Example 3.

Within separate aspects, the present invention provides a variety of in vitro uses for the compounds provided herein. For example, such compounds may be used as probes for the detection and localization of GABA$_A$ receptors, in samples such as tissue sections, as positive controls in assays for receptor activity, as standards and reagents for determining the ability of a candidate agent to bind to GABA$_A$ receptor, or as radiotracers for positron emission tomography (PET) imaging or for single photon emission computerized tomography (SPECT). Such assays can be used to characterize GABA$_A$ receptors in living subjects. Such compounds are also useful as standards and reagents in determining the ability of a potential pharmaceutical to bind to GABA$_A$ receptor.

Within methods for determining the presence or absence of GABA$_A$ receptor in a sample, a sample may be incubated with a compound as provided herein under conditions that permit binding of the compound to GABA$_A$ receptor. The amount of compound bound to GABA$_A$ receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of capsaicin receptor in the sample. Detection assays, including receptor autoradiography (receptor mapping) of GABA$_A$ receptors in cultured cells or tissue samples may be performed as described by Kuhar in sections 8.1.1 to 8.1.9 of Current Protocols in Pharmacology (1998) John Wiley & Sons, New York.

For example, compounds provided herein may be used for detecting GABA$_A$ receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of RO15-1788 to GABA$_A$ receptors within cell and tissue samples) at least one of the matched cell or tissue samples that has not previously been contacted with any compound provided herein with an experimental solution comprising a detectably-labeled preparation of the selected compound at the first measured molar concentration. The control sample is prepared in the same manner as the experimental sample and also contains an unlabelled preparation of the same compound at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of GABA$_A$ receptor in the experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

Compounds provided herein may also be used within a variety of well known cell culture and cell separation methods. For example, compounds may be linked to the interior surface of a tissue culture plate or other cell culture support, for use in immobilizing GABA$_A$ receptor-expressing cells for screens, assays and growth in culture. Such linkage may be performed by any suitable technique, such as the methods described above, as well as other standard techniques. Compounds may also be used to facilitate cell identification and sorting in vitro, permitting the selection of cells expressing a GABA$_A$ receptor. Preferably, the compound(s) for use in such methods are labeled as described herein. Within one embodiment, a compound linked to a fluorescent marker, such as fluorescein, is contacted with the cells, which are then analyzed by fluorescence activated cell sorting (FACS).

Within other aspects, methods are provided for modulating binding of ligand to a GABA$_A$ receptor in vitro or in vivo, comprising contacting a GABA$_A$ receptor with a sufficient amount of a compound provided herein, under conditions suitable for binding of ligand to the receptor. The GABA$_A$ receptor may be present in solution, in a cultured or isolated cell preparation or within a patient. Preferably, the GABA$_A$ receptor is a present in the brain of a mammal. In general, the amount of compound contacted with the receptor should be sufficient to modulate ligand binding to GABA$_A$ receptor in vitro within, for example, a binding assay as described in Example 3.

Also provided herein are methods for altering the signal-transducing activity of cellular GABA$_A$ receptor (particularly the chloride ion conductance), by contacting GABA$_A$ receptor, either in vitro or in vivo, with a sufficient amount of a compound as described above, under conditions suitable for binding of ligand to the receptor. The GABA$_A$ receptor may be present in solution, in a cultured or isolated cell preparation or within a patient, and the amount of compound may be an amount that would be sufficient to alter the signal-transducing activity of GABA$_A$ receptors in vitro. In general, the amount of compound contacted with the receptor should be sufficient to modulate ligand binding to GABA$_A$ receptor in vitro within, for example, a binding assay as described in Example 3. An effect on signal-transducing activity may be assessed as an alteration in the electrophysiology of the cells, using standard techniques. If the receptor is present in an animal, an alteration in the electrophysiology of the cell may be detected as a change in the animal's feeding behavior. The amount of a compound that would be sufficient to alter the signal-transducing activity of GABA$_A$ receptors may be determined via a GABA$_A$ receptor signal transduction assay, such as the assay described in Example 4. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of GABA$_A$ receptors in vitro may be determined from a detectable change in the electrophysiology of cells expressing GABA$_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing GABA$_A$ receptors has occurred.

The following Examples are offered by way of illustration and not by way of limitation. Unless otherwise specified all reagents and solvent are of standard commercial grade and are used without further purification. Starting materials and various intermediates may be obtained from commercial sources, prepared from commercially available organic compounds, or prepared using well known synthetic methods.

EXAMPLES

Example 1

Preparation of Representative Imidazolylmethyl Pyridines

This Example illustrates the synthesis of 2-[2-(6-fluoro-pyridin-2-yl)-imidazol-1-yl methyl]-3,5-diethoxy-pyridine (compound 4), a representative imidazolylmethyl pyridine.

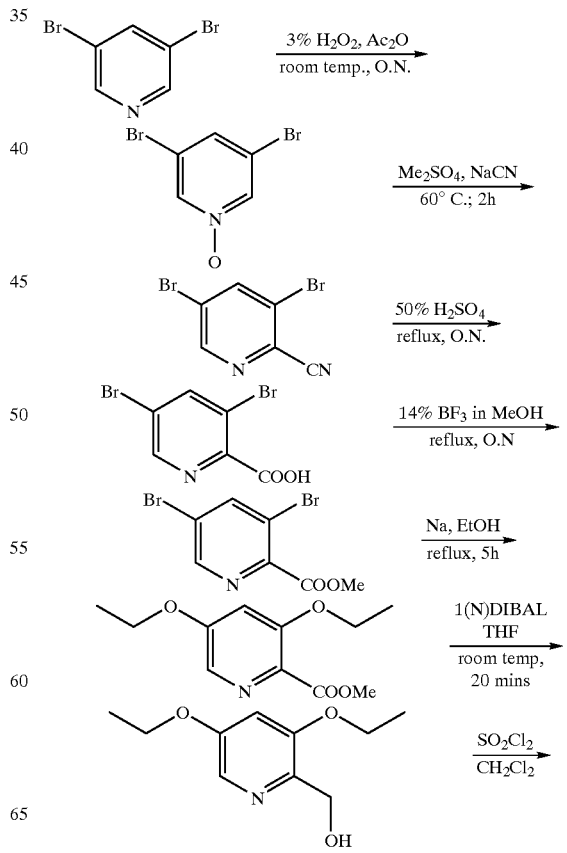

-continued

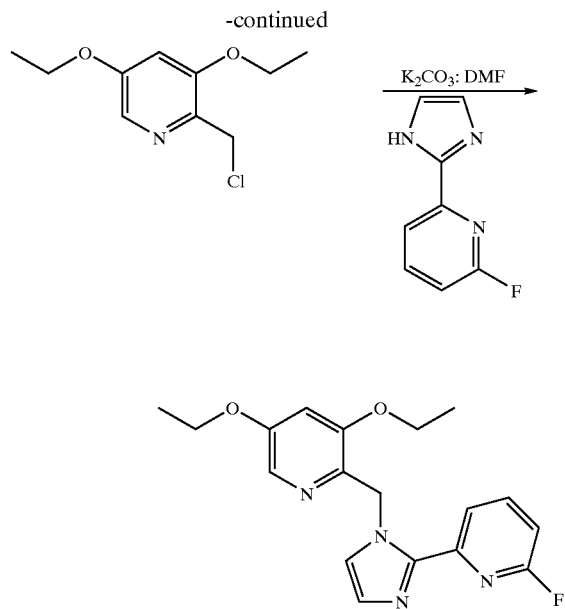

1. Preparation of 3,5-Diethoxy-pyridine-2-carboxylic acid ethyl ester 3,5-dibromo-pyridine-2-carboxylic acid methyl ester is prepared using published protocols (*Bull. Chem. Soc.* Japan (1970) 43:3210–3214), as summarized above. To a stirred solution of Na (78 mg, 3.39 mmol) in EtOH (5 mL), 3,5-dibromo-pyridine-2-carboxylic acid methyl ester (0.5 g, 1.69 mmol) is added, and refluxed for 5 hours. After evaporation of most of the solvent under reduced pressure, the residue is neutralized with saturated $NH_4Cl$ solution, extracted with EtOAc, washed with brine, dried over $Na_2SO_4$, and concentrated. The organic residue is purified with 50% EtOAc/hexanes to afford 3,5-diethoxy-pyridine-2-carboxylic acid ethyl ester as a viscous liquid (250 mg, 60%); $^1$H NMR (300 MHz, $CDCl_3$): 7.97 (s, 1H), 6.79 (s, 1H), 4.41 (q, J=6.9 Hz, 2H), 4.15 (q, J=6.9 Hz, 2H), 3.65 (q, J=6.9 Hz, 2H), 1.45 (t, J=6.9 Hz, 6H), 1.15 (t, J=6.9 Hz, 6H).

2. Preparation of (3, 5-Diethoxy-pyridin-2-yl)-methanol

To the 3,5-diethoxy-pyridine-2-carboxylic acid ethyl ester solution (250 mg, 1.04 mmol) in $CH_2Cl_2$ (10 ml), a solution of DIBAL in THF (1N, 3 mL) is added, and stirred at room temperature for 20 minutes. Excess reagent is quenched with Glauber's salt ($Na_2H_2SO_4 \cdot 10H_2O$), filtered and concentrated to afford (3,5-diethoxy-pyridin-2-yl)-methanol (166 mg, 80% yield); $^1$H NMR (300 MHz, $CDCl_3$): 7.77 (s, 1H), 6.69 (s, 1H), 4.65 (s, 2H), 4.15 (q, J=6.9 Hz, 2H), 3.65 (q, J=6.9 Hz, 2H), 1.45 (t, J=6.9 Hz, 6H).

3. Preparation of 2-Chloromethyl-3,5-diethoxy-pyridine

To a solution of (3,5-diethoxy-pyridin-2-yl)-methanol (166 mg, 0.84 mmol) in $CH_2Cl_2$ (5 mL) is added 2.0 M solution of $SOCl_2$ (1 mL) in $CH_2Cl_2$. The reaction mixture is stirred at room temperature for 30 minutes, diluted with toluene and concentrated to afford 2-chloromethyl-3,5-diethoxy-pyridine as HCl salt which is directly used for the next step.

4. Preparation of 2-[2-(6-Fluoro-pyridin-2-yl)-imidazol-1-yl methyl] -3,5-diethoxy-pyridine (Compound 4)

To a solution of 2-chloromethyl-3,5-diethoxy-pyridine (174 mg, 0.69 mmol) in DMF (5 mL) is added 2-fluoro-6-(1H-imidazol-2-yl)-pyridine (112 mg, 0.69 mmol), and the reaction is stirred at room temperature overnight. The reaction mixture is diluted with water, extracted with EtOAc, washed with brine, dried over $Na_2SO_4$, and concentrated. The residue is purified by column chromatography eluting with 8% MeOH—$CH_2Cl_2$ containing few drops of $NH_4OH$ to afford 2-[2-(6-fluoro-pyridin-2-yl)-imidazol-1-yl methyl]-3,5-diethoxy-pyridine (118 mg, 49%); $^1$H NMR (300 MHz, $CDCl_3$): 8.06 (dd, J=5.1, 2.4 Hz, 1H), 7.81 (t, J=7.9 Hz, 1H), 7.75 (d, J=2.4 Hz, 1H), 7.09 (s, 1H), 7.04 (s, 1H), 6.80 (dd, J=5.1, 2.7 Hz, 1H), 6.65 (d, J= 2.4 Hz, 1H), 5.95 (s, 2H), 4.02 (q, J=6.9 Hz, 2H), 3.90 (q, J= 6.9 Hz, 2H), 1.39 (t, J=6.9 Hz, 2H), 1.16 (t, J=6.9 Hz, 2H), m/z 343 [M+1].

Example 2

Preparation of Representative Imidazolylmethyl Pyrazines

This Example illustrates the synthesis of representative imidazolylmethyl pyrazines.

A. 2-[2-(6-Fluoro-pyridin-2-yl)-imidazol-1-ylmethyl]-3-methoxy-5-phenyl-pyrazine (Compound 1)

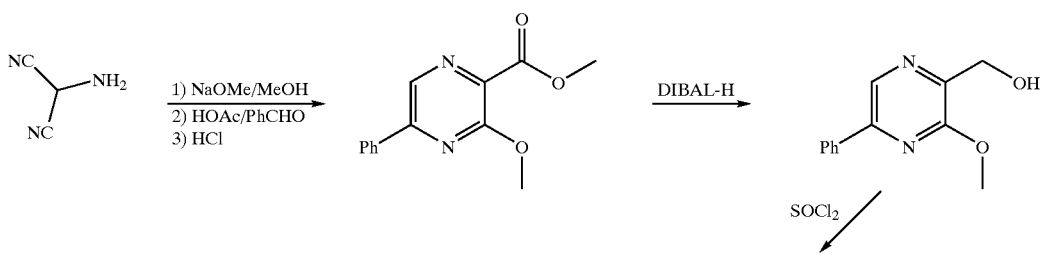

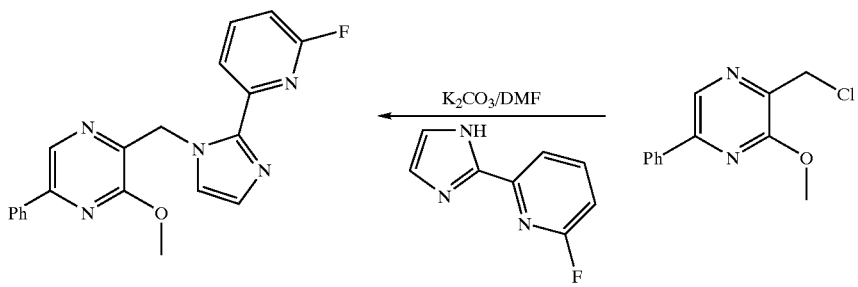

1. Preparation of 3-Methoxy-5-phenyl-pyrazine-2-carboxylic acid methyl ester

To a solution of 2-amino-malononitrile 4-toluenesufonate (5.0 g, 19.3 mmol) in methanol (60 mL) at room temperature under $N_2$ is added NaOMe (25% w/w in MeOH, 5.2 mL, 22.7 mmol). After 2 hours, acetic acid (0.204 g, 3.4 mmol) is added. The mixture is cooled to 0° C. and to the mixture is added benzaldehyde (3 g, 19.9 mmol). The mixture is stirred at this temperature for an additional 2 hours and then gradually warmed to room temperature overnight. To the mixture is added concentrated HCl (9.2 g, 80 mmol) and the mixture is stirred at room temperature over the weekend. Solvent is removed in vacuo. To the crude mixture is added saturated $NH_4Cl$ (50 mL) and DCM (100 mL). The organic layer is separated and the aqueous layer is extracted (2×50 mL) with DCM. The combined organic layers are dried and solvent removed. Column chromatography separation (silica gel, DCM) gives 1.0 g of 3-methoxy-5-phenyl-pyrazine-2-carboxylic acid methyl ester as a yellow solid.

2. Preparation of (3-Methoxy-5-phenyl-pyrazin-2-yl)-methanol

To a solution of 3-methoxy-5-phenyl-pyrazine-2-carboxylic acid methyl ester (150 mg, 0.58 mmol) in THF (20 mL) is added DIBAL-H (1 M in DCM, 1 mL, 1 mmol) dropwise at 0° C. under $N_2$. The mixture is stirred at this temperature for 0.5 hour. Another portion of DIBAL-H (1 M in DCM, 0.8 mL, 0.8 mmol) is added. After 0.5 hour, the reaction is quenched with saturated $NH_4Cl$ (1 mL), and then NaOH (1.5 M, 2 mL). The mixture is extracted with EtOAc (3×20 mL). The combined organic layers are dried and the solvent removed. The crude product is purified by PTLC (silica gel; 10% MeOH in DCM) to give 60 mg of (3-methoxy-5-phenyl-pyrazin-2-yl)-methanol as an oil.

3. Preparation of 2-Chloromethyl-3-methoxy-5-phenyl-pyrazine

To a solution of (3-methoxy-5-phenyl-pyrazin-2-yl)-methanol (60 mg, 0.28 mmol) in DCM (5 mL) is added $SOCl_2$ (5 eq) at room temperature. The mixture is stirred at room temperature for an additional one hour. Solvent and volatile materials are removed in vacuo to dryness to give 65 mg of 2-chloromethyl-3-methoxy-5-phenyl-pyrazine as an oil.

4. Preparation of 2-Fluoro-6-(1H-imidazol-2-yl)-pyridine
   a. Preparation of 2-Fluoropyridine-6-carboxaldehyde To a solution of diisopropylamine (6.54 mL, 1.2 equiv) in 30 mL of THF at 0° C., a solution of n-butyllithium (17.1 mL, 2.5M in hexanes) is added dropwise. Stirring is continued for 15 minutes at 0° C., the reaction is then cooled to −78° C. 2-Fluoro-6-methylpyridine (4.00 mL, 38.9 mmol) is added dropwise to the cold solution. The reaction mixture is stirred at −78° C. for 1 hours and then quenched with DMF (4.52 mL, 1.5 equiv). The reaction is maintained at −78° C. for 30 minutes and then warmed to 0° C. The cold solution is added to a mixture of sodium periodate (24.9 g) in 120 mL of water at 0° C. The reaction mixture is allowed to gradually warm to room temperature over 1 hours and then stirred at room temperature for 24 hours. The reaction mixture is filtered through a plug of celite to remove the precipitate and the plug is washed with ether. The organic layer is separated, washed with aqueous sodium bicarbonate (1×40 mL), then with 0.25M $KH_2PO_4$ (1×40 mL) and then brine (1×40 mL). The organic solution is dried ($NaSO_4$) and concentrated in vacuo.

b. Preparation of 2-Fluoro-6-(1H-imidazol-2-yl)-pyridine

To a solution of the crude aldehyde from step a (above) in methanol (12 mL) aqueous glyoxal (6.21 mL, 40 wt. % in water) is added dropwise. The solution is cooled to 0° C. and aqueous ammonium hydroxide (6.0 mL, 28 wt. % in water) is added. The reaction is allowed to warm to room temperature gradually over about an hour and then stirred another 3 h at room temperature. Most of the methanol is removed in vacuo, the reaction mixture diluted with water (10 mL) and extracted with ethyl acetate (30 mL). The organic layer is washed with brine (20 mL), diluted with hexanes (15 mL), passed through a plug of silica gel (¼ inch deep×1¼ inch diameter), and the plug washed with more 2:1 ethyl acetate/hexanes (20 mL) The combined eluents are concentrated in vacuo to yield crude 2-Fluoro-6-(1H-imidazol-2-yl)-pyridine.

5. Prepapation of 2-[2-(6-Fluoro-pyridin-2-yl)-imidazol-1-ylmethyl]-3-methoxy-5-phenyl-pyrazine (Compound 1)

A mixture of 2-chloromethyl-3-methoxy-5-phenyl-pyrazine (70 mg, 0.30 mmol), 2-fluoro-6-(1H-imidazol-2-yl)-pyridine (48 mg, 0.294 mmol) and $K_2CO_3$ (123 mg, 0.9 mmol) in DMF (5 mL) is stirred at 45° C. for 16 hours. On cooling, the reaction is quenched with saturated $NH_4Cl$ (2 mL) and extracted with DCM (3×10 mL). The combined organic layers are dried and solvent removed. PTLC separation (10% MeOH in DCM) gives 91 mg of 2-[2-(6-fluoro-pyridin-2-yl)-imidazol-1-ylmethyl]-3-methoxy-5-phenyl-pyrazine as an oil. $^1$H NMR ($CDCl_3$) 8.41 (s, 1H), 8.08 (dd, 1H), 7.95–7.99 (m, 2H), 7.80 (dd, 1H), 7.42–7.49 (m, 3H), 7.22 (s, 1H), 7.15 (s, 1H), 6.77 (dd, 1H), 5.98 (s, 2H), 4.08 (s, 3H).

B. 3-Methoxy-5-phenyl-2-(2-thiazol-2-yl-imidazol-1-ylmethyl)-pyrazine (Compound 2)

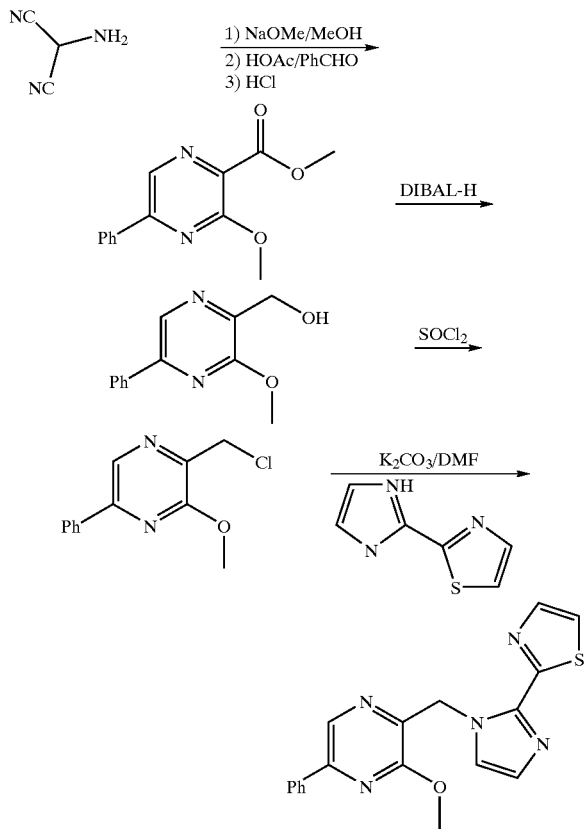

1. Synthesis of 2-(1H-imidazol-2-yl)-thiazole

a. Preparation of 1-ethoxymethyl-2-tributylstannanyl-1H-imidazole 1.6 M n-BuLi (12.0 mL, 19.2 mmol) is slowly added to a solution of 1-ethoxymethyl-1H-imidazole (2.20 g, 17.4 mmol; prepared essentially as described by Tang, et al. (1978) *J. Am. Chem. Soc.* 100:3918) in THF (30 mL) at −78° C. under $N_2$. The reaction mixture is stirred at −78° C. for 20 minutes, whereupon tributyltin chloride (5.7 mL, 20.9 mmol) is slowly added. The reaction mixture is stirred at −78° C. for 10 minutes, and then warmed to room temperature. After stirring at room temperature for 1.5 hours, the reaction mixture is concentrated in vacuo. The residue is triturated with hexanes and filtered, and the filtrate is concentrated in vacuo. The residue is again triturated with hexanes and filtered, and the filtrate concentrated in vacuo. The $^1$H NMR of the resulting oil indicates a 2:1 mixture of 1-ethoxymethyl-2-tributylstannanyl-1H-imidazole: 1-ethoxymethyl-1H-imidazole. This material is used in the next reaction without further purification. Selected $^1$H NMR resonances (400 MHz, $CDCl_3$) δ 7.21 (s, 1H), 7.14 (s, 1H), 5.24 (s, 2H) ppm.

b. Preparation of 2-(1-ethoxymethyl-1H-imidazol-2-yl)-thiazole

A solution of crude 1-ethoxymethyl-2-tributylstannanyl-1H-imidazole (previous experimental), 2-bromothiazole (1.05 mL, 11.6 mmol, 1.0 eq based on integration of $^1$H NMR of crude 1-ethoxymethyl-2-tributylstannanyl-1H-imidazole), and $Pd(PPh_3)_4$ (0.67 g, 0.58 mmol) in toluene (20 mL) is stirred at 80° C. for 18 hours. After cooling to room temperature, the reaction mixture is poured into saturated aqueous $NaHCO_3$ and extracted twice with $CH_2Cl_2$. The combined extracts are dried over $Na_2SO_4$ and concentrated in vacuo. The residue is purified by flash chromatography on silica gel, eluting with 2:1 hexanes-EtOAc (+0.5% $Et_3N$). Fractions containing product are concentrated and resubjected to flash chromatography on silica gel. Elution with 2:1 hexanes-EtOAc (+0.5% $Et_3N$) affords (26%) of 2-(1-ethoxymethyl-1H-imidazol-2-yl)-thiazole as a bright yellow oil. $^1$H NMR (400 MHz, $CDCl_3$) δ 7.82 (d, J=3.2 Hz, 1H), 7.33 (d, J=3.2 Hz, 1H), 7.20 (d, J=1.2 Hz, 1H), 7.15 (d, J=1.2 Hz, 1H), 6.03 (s, 2H), 3.56 (q, J=7.2 Hz, 2H) 1.17 (t, J=7.2 Hz, 3H) ppm.

c. Preparation of 2-(1H-imidazol-2-yl)-thiazole

Concentrated HCl (10 ml) is added to a solution of 2-(1-ethoxymethyl-1H-imidazol-2-yl)-thiazole (940 mg, 4.49 mmol) in 24 mL of 1:1 EtOH-$H_2O$ at room temperature. The solution is stirred at reflux for 3 hours. The reaction mixture is then cooled to 0° C. and made basic by the addition of about 12 mL of 10 N aqueous NaOH. The mixture is back titrated to approximately pH 4 using concentrated HCl. Solid $NaHCO_3$ is added to the point of saturation and approximately pH 8. The mixture is then extracted twice using a mixture of THF and EtOAc. The combined extracts are dried over $Na_2SO_4$ and concentrated to an oily solid, which is triturated with a small amount of $CH_2Cl_2$. The solid is collected by filtration. The filtrate is concentrated, and the oily solid triturated once more with $CH_2Cl_2$. The second resultant solid is collected by filtration and combined with the solid first obtained. The product, 2-(1H-imidazol-2-yl)-thiazole, is obtained as a slightly off-white solid. $^1$H NMR (400 MHz, DMSO-$d_6$) δ 13.04 (br, 1H), 7.87 (d, J=3.2 Hz, 1H), 7.70 (d, J=3.2 Hz, 1H), 7.14 (br, 2H) ppm.

2. Synthesis of 3-methoxy-5-phenyl-2-(2-thiazol-2-yl-imidazol-1-ylmethyl)-pyrazine (Compound 2)

A mixture of 2-chloromethyl-3-methoxy-5-phenyl-pyrazine (90 mg, 0.38 mmol; prepared as described above), 2-(1H-imidazol-2-yl)-thiazole (55 mg, 0.363 mmol) and $K_2CO_3$ (159 mg, 1.15 mmol) in DMF (7 mL) is stirred at 45° C. for 16 hours. On cooling, the reaction is quenched with saturated $NH_4Cl$ (3 mL) and extracted with DCM (3×15 mL). The combined organic layers are dried and solvent removed. PTLC separation (silica gel; 10% MeOH in DCM) gives 78 mg of 3-methoxy-5-phenyl-2-(2-thiazol-2-yl-imidazol-1-ylmethyl)-pyrazine as an oil. $^1$H NMR ($CDCl_3$) 8.47 (s, 1H), 7.97–8.01 (m, 2H), 7.76 (d, 1H), 7.42–7.49 (m, 3H), 7.28 (d, 1H), 7.18 (s, 1H), 7.06 (s, 1H), 6.03 (s, 2H), 4.05 (s, 3H)

Additional compounds may be prepared as described generally in the following scheme, and in more detail below:

33 34
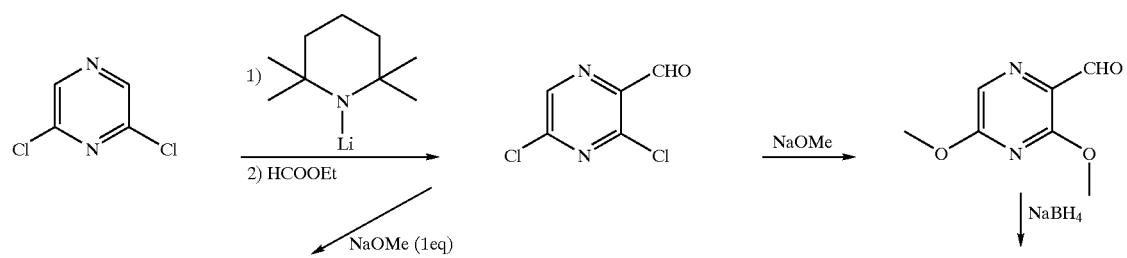
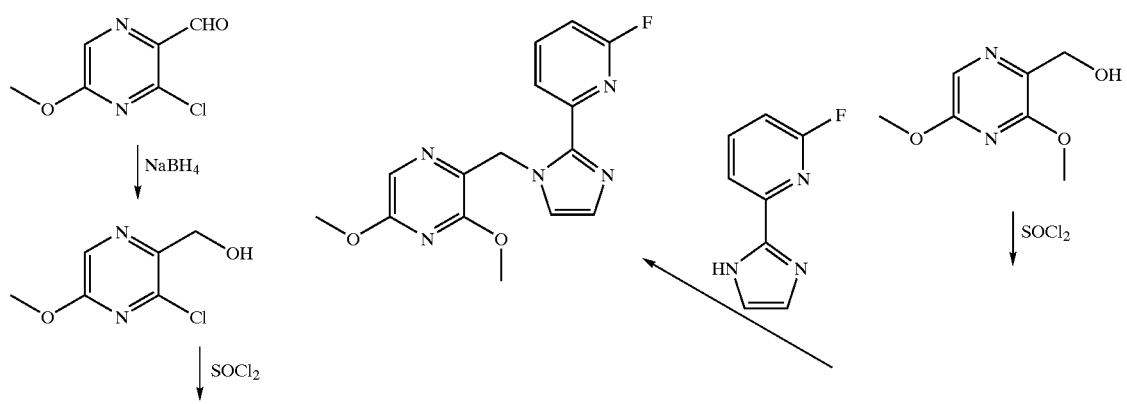
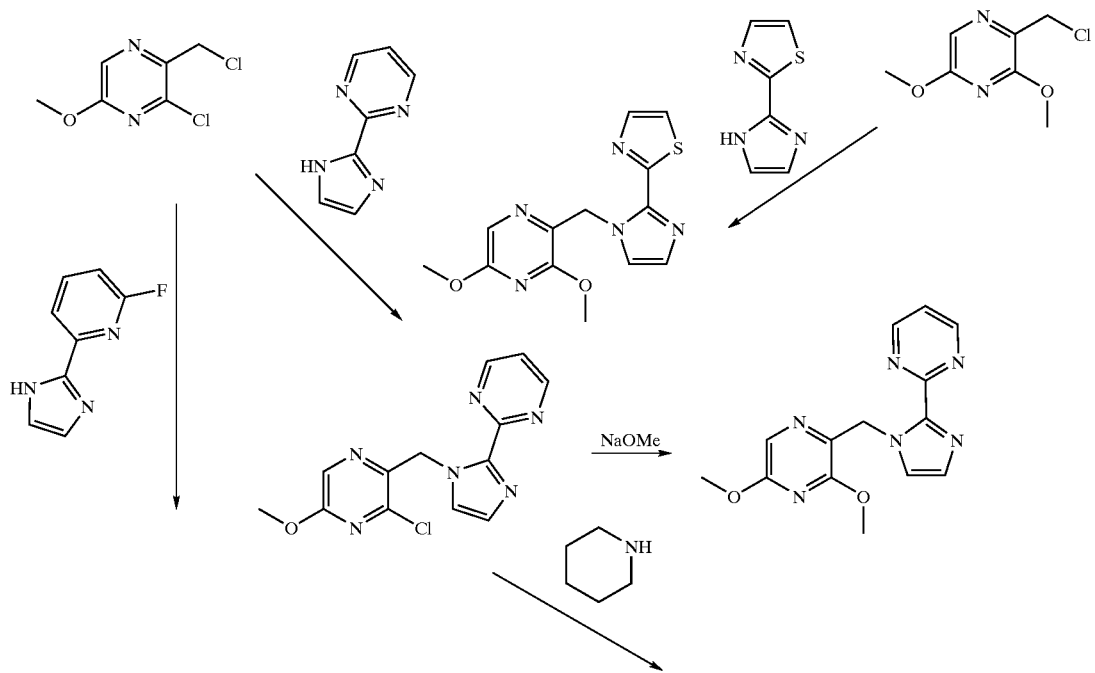

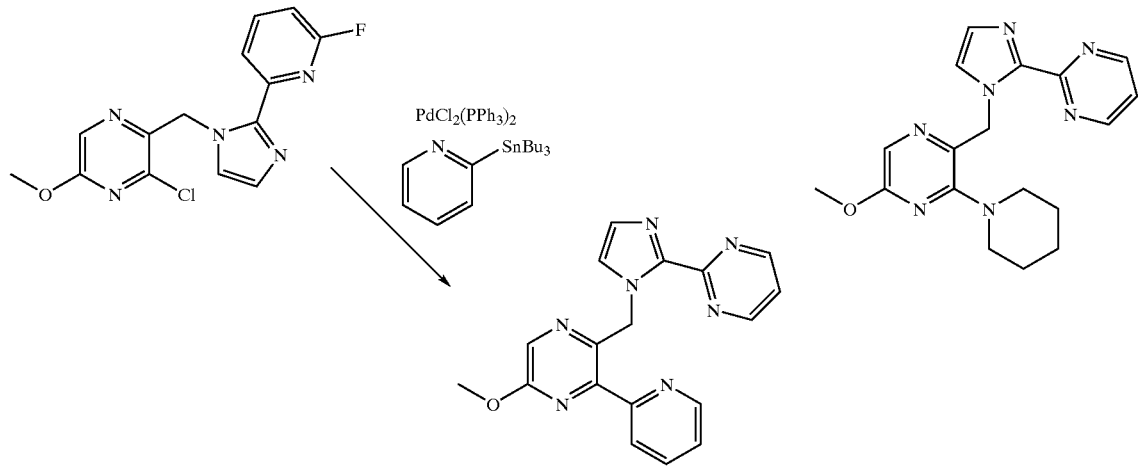

C. 2-[2-(6-Fluoro-pyridin-2-yl)-imidazol-1-ylmethyl]-3,5-dimethoxy-pyrazine (Compound 3)

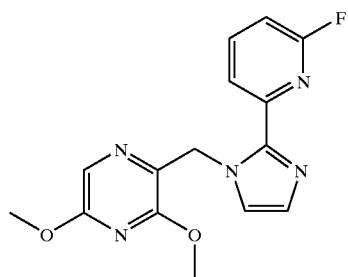

1. Preparation of 3,5-Dichloro-pyrazine-2-carbaldehyde

To THF (200 mL) at −30° C. under $N_2$ is added n-butyllithium (2.5 M in hexane, 8 mL, 20 mmol), followed by 2,2,6,6-tetramethylpiperidine (3.5 mL, 20.5 mmol). The mixture is warmed to room temperature and stirred at this temperature for 10 minutes. After the mixture is cooled to −78° C., 2,6-dichloropyrazine (2.5 g, 16.75 mmol) in THF (25 mL) is added and the mixture is stirred at this temperature for 1 hour. To the mixture is added ethyl formate (2 mL, 24.4 mmol) and the mixture is stirred at this temperature for an additional 2 hours. The reaction is quenched with saturated $NH_4Cl$ (25 mL), warmed to room temperature, and diluted with ethyl acetate (200 mL). The organic layer is separated and dried, and solvent removed. Column chromatography on silica gel (15% ethyl acetate in hexane) gives 2.4 g of 3,5-dichloro-pyrazine-2-carbaldehyde as an oil.

2. Preparation of 3, 5-Dimethoxy-pyrazine-2-carbaldehyde

To a solution of 3,5-dichloro-pyrazine-2-carbaldehyde (150 mg, 0.85 mmol) in methanol (5 mL) is added sodium methoxide (25% w/w in MeOH, 458 mg, 2.1 mmol). After the mixture is stirred at room temperature over night, the reaction is quenched with saturated $NH_4Cl$ (1 mL) and solvent removed in vacuo until dryness. DCM (20 mL) is added, and the solution is dried and solvent removed to give 140 mg of 3,5-dimethoxy-pyrazine-2-carbaldehyde as an oil.

3. Preparation of (3,5-Dimethoxy-pyrazin-2-yl)-methanol

To a solution of 3,5-dimethoxy-pyrazine-2-carbaldehyde (120 mg, 0.71 mmol) in MeOH (8 mL) is added sodium borohydride (40 mg, 1.1 mmol) at 0° C. After the mixture is stirred at this temperature for 0.5 hour, the reaction is quenched with saturated $NH_4Cl$ (0.7 mL) and solvent removed in vacuo until dryness. DCM (20 mL) is added, and the solution is dried and solvent removed to give 118 mg of (3,5-dimethoxy-pyrazin-2-yl)-methanol as an oil.

4. Preparation of 2-Chloromethyl-3,5-dimethoxy-pyrazine

To a solution of (3,5-dimethoxy-pyrazin-2-yl)-methanol (100 mg, 0.59 mmol) in DCM (5 mL) was added $SOCl_2$ (5 eq) at room temperature. The mixture is stirred at room temperature for an additional one hour. Solvent and volatile materials are removed in vacuo to dryness to give 110 mg of 2-chloromethyl-3,5-dimethoxy-pyrazine as an oil.

5. Preparation of 2-[2-(6-Fluoro-pyridin-2-yl)-imidazol-1-ylmethyl] -3,5-dimethoxy-pyrazine (Compound 3)

A mixture of 2-chloromethyl-3,5-dimethoxy-pyrazine (115 mg, 0.61 mmol), 2-fluoro-6-(1H-imidazol-2-yl)-pyridine (98 mg, 0.60 mmol) and $K_2CO_3$ (250 mg, 1.81 mmol) in DMF (7 mL) is stirred at 45° C. for 16 hours. On cooling, the reaction is quenched with saturated $NH_4Cl$ (3 mL) and extracted with DCM (3×15 mL). The combined organic layers are dried and solvent removed. PTLC (silica gel) separation (10% MeOH in DCM) gives 123 mg of 2-[2-(6-fluoro-pyridin-2-yl)-imidazol-1-ylmethyl] -3,5-dimethoxy-pyrazine as an oil. LRMS calcd 315.30, found 316.20 (MH+).

D. 3,5-Dimethoxy-2-(2-thiazol-2-yl-imidazol-1-ylmethyl)-pyrazine1 (Compound 5)

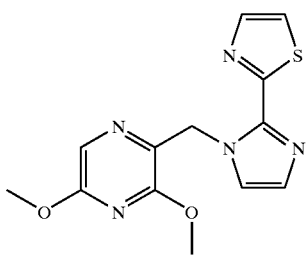

A mixture of 2-chloromethyl-3,5-dimethoxy-pyrazine (140 mg, 0.74 mmol), 2-(1H-imidazol-2-yl)-thiazole (106 mg, 0.70 mmol) and $K_2CO_3$ (307 mg, 2.22 mmol) in DMF (10 mL) is stirred at 45° C. for 16 hours. On cooling, the reaction is quenched with saturated $NH_4Cl$ (5 mL) and extracted with DCM (3×15 mL). The combined organic layers are dried and solvent removed. PTLC (silica gel) separation (10% MeOH in DCM) gives 170 mg of 3,5-dimethoxy-2-(2-thiazol-2-yl-imidazol-1-ylmethyl)-pyrazine as an oil. $^1$H NMR ($CDCl_3$) 7.80 (d, 1H), 7.68 (s, 1H), 7.32 (d, 1H), 7.09 (s, 1H), 6.98 (s, 1H), 5.97 (s, 2H), 3.92 (s, 3H) 3.87 (s, 3H).

E. 3-Chloro-2-[2-(6-fluoro-pyridin-2-yl)-imidazol-1-ylmethyl]-5-methoxy-pyrazine (Compound 6)

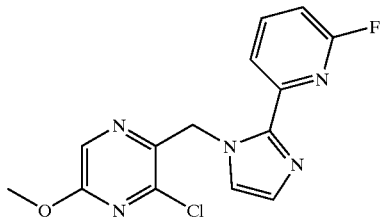

1. Preparation of 3-Chloro-5-methoxy-pyrazine-2-carbaldehyde

To a solution of 3,5-dichloro-pyrazine-2-carbaldehyde (150 mg, 0.85 mmol) in methanol (5 mL) is added sodium methoxide (25% w/w in MeOH, 183 mg, 0.85 mmol) at 0° C. After the mixture is stirred at 0° C. for 2 hours and then at room temperature overnight, the reaction is quenched with saturated $NH_4Cl$ (1 mL) and solvent removed in vacuo until dryness. DCM (20 mL) is added, and the solution is dried and solvent removed to give 140 mg of 3-chloro-5-methoxy-pyrazine-2-carbaldehyde as an oil.

2. Preparation of (3-Chloro-5-methoxy-pyrazin-2-yl)-methanol

To a solution of 3-chloro-5-methoxy-pyrazine-2-carbaldehyde (560 mg, 3.24 mmol) in MeOH (15 mL) is added sodium borohydride (183 mg, 4.83 mmol) at 0° C. After the mixture is stirred at this temperature for 0.5 hour, the reaction is quenched with saturated $NH_4Cl$ (1 mL) and solvent removed in vacuo until dryness. DCM (50 mL) is added, and the solution is dried and solvent removed to give 550 mg of (3-chloro-5-methoxy-pyrazin-2-yl)-methanol as an oil.

3. Preparation of 3-Chloro-2-chloromethyl-5-methoxy-pyrazine

To a solution of (3-chloro-5-methoxy-pyrazin-2-yl)-methanol (100 mg, 0.57 mmol) in DCM (5 mL) was added $SOCl_2$ (5 eq) at room temperature. The mixture is stirred at room temperature for an additional one hour. Solvent and volatile materials are removed in vacuo to dryness to give 110 mg of 3-chloro-2-chloromethyl-5-methoxy-pyrazine as an oil.

4. Preparation of 3-Chloro-2-[2-(6-fluoro-pyridin-2-yl)-imidazol-1-ylmethyl]-5-methoxy-pyrazine (Compound 6)

A mixture of 3-chloro-2-chloromethyl-5-methoxy-pyrazine (350 mg, 1.81 mmol), 2-fluoro-6-(1H-imidazol-2-yl)-pyridine (266 mg, 1.63 mmol) and $K_2CO_3$ (750 mg, 5.43 mmol) in DMF (10 mL) is stirred at 45° C. for 16 hours. On cooling, the reaction is quenched with saturated $NH_4Cl$ (3 mL) and extracted with DCM (3×20 mL). The combined organic layers are dried and solvent removed. PTLC (silica gel) separation (10% MeOH in DCM) gives 370 mg of 3-chloro-2-[2-(6-fluoro-pyridin-2-yl)-imidazol-1-ylmethyl]-5-methoxy-pyrazine as an oil. $^1$H NMR ($CDCl_3$) 8.08–8.14 (m, 1H), 7.98(s, 1H), 7.81 (dd, 1H), 7.20 (s, 1H), 7.07 (s, 1H), 6.80 (dd, 1H), 6.02 (s, 2H), 3.98 (s, 3H)

F. Synthesis of 2-[2-(6-Fluoro-pyridin-2-yl)-imidazol-1-ylmethyl]-5-methoxy-3-pyridin-2-yl-pyrazine (Compound 7)

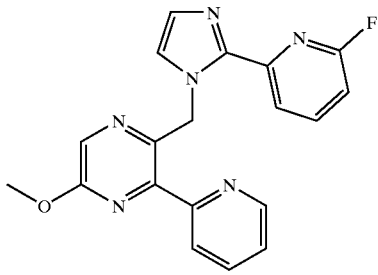

A mixture of 3-chloro-2-[2-(6-fluoro-pyridin-2-yl)-imidazol-1-ylmethyl]-5-methoxy-pyrazine (80 mg, 0.25 mmol), 2-tributylstannylpyridine (138 mg, 0.37 mmol), and $PdCl_2(PPh_3)_2$ (18 mg, 0.026 mmol) in toluene (10 mL) is heated at 110° C. in a sealed tube for 16 hours. On cooling, the mixture is diluted with DCM (20 mL) and filtered. After the solvent is removed, the residue is purified by PTLC (silica gel; 5% MeOH in DCM) to give 78 mg of 2-[2-(6-fluoro-pyridin-2-yl)-imidazol-1-ylmethyl]-5-methoxy-3-pyridin-2-yl-pyrazine. $^1$H NMR ($CDCl_3$) 8.59 (d, 1H), 8.15 (d, 1H), 8.08 (s, 1H), 8.02 (d, 1H), 7.85(t, 1H), 7.72 (dd, 1H), 7.32 (dd, 1H), 7.10 (s, 1H), 7.15 (s, 1H), 6.65 (dd, 1H), 6.31 (s, 2H), 4.01 (s, 3H).

G. 2-[1-(3-Chloro-5-methoxy-pyrazin-2-ylmethyl)-1H-imidazol-2-yl]-pyrimidine (Compound 8)

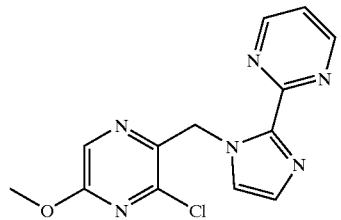

1. Synthesis of 2-(1H-imidazol-2-yl)-pyrimidine hydrochloride

A mixture of 2-Cyanopyrimidine (8.0 g, 76 mmol, prepared essentially according to Liebigs Ann. Chem. 2, 1981, 333–341) and Aminoacetaldehyde dimethyl acetal (8 g, 76 mmol) is heated at 100° C. for 4 hours, cooled, and 100 mL of MeOH and 5 mL of concentrated HCl are added. The mixture is heated at reflux with stirring for 30 hours, cooled and evaporated to dryness in vacuo. 50 mL of i-PrOH is added to the residue and the mixture is heated at reflux with stirring for 30 minutes and cooled. The crystals are collected by filtration, washed with ether, and dried to give the title compound. $^1$H NMR (DMSO): 9.08 (d, 2H), 7.87 (s, 2H), 7.75 (t, 1H). LRMS calcd 146, found 147 (MH+).

2. Synthesis of 2-[1-(3-Chloro-5-methoxy-pyrazin-2-ylmethyl)-1H-imidazol-2-yl]-pyrimidine (Compound 8)

A mixture of 3-chloro-2-chloromethyl-5-methoxy pyrazine (141 mg, 0.73 mmol), 2-(1H-imidazol-2-yl)-pyrimidine (105 mg, 0.72 mmol) and $K_2CO_3$ (307 mg, 2.22 mmol) in DMF (10 mL) is stirred at 45° C. for 16 hours. On cooling, the reaction is quenched with saturated $NH_4Cl$ (5 mL) and extracted with DCM (3×15 mL). The combined organic layers are dried and solvent removed. PTLC separation (silica gel; 10% MeOH in DCM) gives 120 mg of 2-[1-(3-chloro-5-methoxy-pyrazin-2-ylmethyl)-1H-imidazol-2-yl]-pyrimidine as an oil. $^1$H NMR ($CDCl_3$) 8.98 (d, 2H), 7.98 (s, 1H), 7.27 (s, 1H), 7.14–7.18 (m, 2H), 6.05 (s, 2H), 3.97 (s, 3H).

H. 2-[1-(3,5-Dimethoxy-pyrazin-2-ylmethyl)-1H-imidazol-2-yl]-pyrimidine (Compound 9)

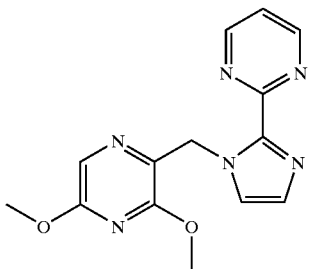

To a solution of 2-[1-(3-chloro-5-methoxy-pyrazin-2-ylmethyl)-1H-imidazol-2-yl]-pyrimidine (30 mg, 0.094 mmol) in THF (5 mL) is added sodium methoxide (25% w/w in methanol, 0.5 mL). The mixture is refluxed for 1 hour. On cooling, saturated $NH_4Cl$ (0.7 mL) is added to quenched the reaction. Solvent is removed in vacuo and to the residue is added DCM (30 mL). The mixture is then dried and solvent removed to give 21 mg of 2-[1-(3,5-dimethoxy-pyrazin-2-ylmethyl)-1H-imidazol-2-yl]-pyrimidine as an oil. 1H NMR ($CDCl_3$) 8.79 (d, 2H), 7.62 (s, 1H), 7.15–7.21 (m, 2H, 7.07 (s, 1H), 5.95 (s, 2H), 3.88 (s, 3H), 3.82 (s, 3H)

I. 2-[1-(5-Methoxy-3-piperidin-1-yl-pyrazin-2-ylmethyl)-1H-imidazol-2-yl]-pyrimidine (Compound 10)

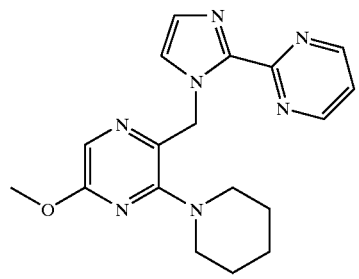

A mixture of 2-[1-(3-chloro-5-methoxy-pyrazin-2-ylmethyl)-1H-imidazol-2-yl]-pyrimidine (30 mg, 0.099 mmol), and piperidine (1 mL) is heated at 110° C. in a sealed tube for 1 hour. On cooling, the volatile materials are removed in vacuo and the residue is purified by PTLC (silica gel; 10% MeOH in DCM) to give 35 mg of 2-[1-(5-Methoxy-3-piperidin-1-yl-pyrazin-2-ylmethyl)-1H-imidazol-2-yl]-pyrimidine. $^1$H NMR ($CDCl_3$) 8.74 (d, 2H), 7.62 (s, 1H), 7.21 s, 1H), 7.08–7.15 (m, 2H), 5.86 (s, 2H), 3.87 (s, 3H), 3.06–3.15 (m, 4H), 1.52–1.66 (m, 6H).

Example 3

Ligand Binding Assay

The high affinity of compounds of this invention for the benzodiazepine site of the $GABA_A$ receptor was confirmed using a binding assay essentially described by Thomas and Tallman (*J. Bio. Chem.* (1981) 156:9838–9842, and *J. Neurosci.* (1983) 3:433–440).

Rat cortical tissue was dissected and homogenized in 25 volumes (w/v) of Buffer A (0.05 M Tris HCl buffer, pH 7.4 at 4° C.). The tissue homogenate was centrifuged in the cold (4° C.) at 20,000×g for 20 minutes. The supernatant was decanted, the pellet rehomogenized in the same volume of buffer, and centrifuged again at 20,000×g. The supernatant of this centrifugation step was decanted and the pellet stored at −20° C. overnight. The pellet was then thawed and resuspended in 25 volumes of Buffer A (original wt/vol), centrifuged at 20,000×g and the supernatant decanted. This wash step was repeated once. The pellet was finally resuspended in 50 volumes of Buffer A.

Incubations contained 100 µl of tissue homogenate, 100 µl of radioligand, (0.5 nM $^3$H-Ro15-1788 [$^3$H-Flumazenil], specific activity 80 Ci/mmol), and test compound or control (see below), and were brought to a total volume of 500 µl with Buffer A. Incubations were carried for 30 min at 4° C. and then rapidly filtered through Whatman GFB filters to separate free and bound ligand. Filters were washed twice with fresh Buffer A and counted in a liquid scintillation counter. Nonspecific binding (control) is determined by displacement of $^3$H Ro15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve was obtained with up to 11 points spanning the compound concentration range from $10^{-12}$M to $10^{-5}$M obtained per curve by the method described above for determining percent inhibition. $K_i$ values were calculated according the Cheng-Prussof equation. Each of the compounds set forth above was tested in this fashion and each was found to have a $K_i$ of <1 µM. Preferred compounds of the invention exhibit $K_i$ values of less than 100 nM and more preferred compounds of the invention exhibit $K_i$ values of less than 10 nM.

Example 4

Electrophysiology

The following assay is used to determine if a compound of the invention acts as an agonist, an antagonist, or an inverse agonist at the benzodiazepine site of the $GABA_A$ receptor.

Assays are carried out essentially as described in White and Gurley (NeuroReport 6:1313–1316, 1995) and White, Gurley, Hartnett, Stirling, and Gregory (Receptors and Channels 3:1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $α_1β_2γ_2$, $α_2β_3γ_2$, $α_3β_3γ_2$, and $α_5β_3γ_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 $\mu$M GABA is applied.

Compounds are evaluated against a GABA concentration that evokes <10% of the maximal evocable GABA current (e.g., 1 $\mu$M-9 $\mu$M). Each oocyte is exposed to increasing concentrations of a compound being evaluated (test compound) in order to evaluate a concentration/effect relationship. Test compound efficacy is calculated as a percent-change in current amplitude: 100* ((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 $\mu$M RO15-1788, followed by exposure to GABA+1 $\mu$M RO15-1788+test compound. Percent change due to addition of compound is calculated as described above. Any percent change observed in the presence of RO15-1788 is subtracted from the percent changes in current amplitude observed in the absence of 1 $\mu$M RO15-1788. These net values are used for the calculation of average efficacy and $EC_{50}$ values by standard methods. To evaluate average efficacy and $EC_{50}$ values, the concentration/effect data are averaged across cells and fit to the logistic equation.

Example 5

MDCK Cytotoxicity Assay

This Example illustrates the evaluation of compound toxicity using a Madin Darby canine kidney (MDCK) cell cytoxicity assay. 1 $\mu$L of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10⁶ cells/ml with warm (37° C.) medium (VITACELL Minimum Essential Medium Eagle, ATCC catalog # 30-2003). 100 $\mu$L of diluted cells is added to each well, except for five standard curve control wells that contain 100 $\mu$L of warm medium without cells. The plate is then incubated at 37° C. under 95% $O_2$, 5% $CO_2$ for 2 hours with constant shaking. After incubation, 50 $\mu$L of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 $\mu$L of serially diluted PACKARD standard is added to each of the standard curve control wells to yield a final concentration in each subsequent well of 200 nM, 100 nM, 50 nM, 25 nM and 12.5 nM. PACKARD substrate solution (50 $\mu$L) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 $\mu$M of a preferred test compound exhibit ATP levels that are at least 80%, preferably at least 90%, of the untreated cells. When a 100 $\mu$M concentration of the test compound is used, cells treated with preferred test compounds exhibit ATP levels that are at least 50%, preferably at least 80%, of the ATP levels detected in untreated cells.

It is to be understood that the foregoing describes preferred embodiments of the present invention and that modifications may be made therein without departing from the spirit or scope of the present invention. Accordingly, the invention is not limited except as by the appended claims.

What is claimed is:

1. A compound of the formula:

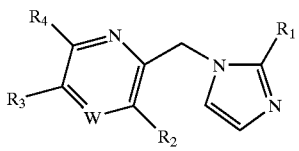

or a pharmaceutically acceptable salt thereof, wherein:
  W represents CH or N;
  $R_1$ represents 5- to 10-membered aryl or heteroaryl, each of which is unsubstituted or substituted with from 1 to 4 groups independently selected from $R_5$;
  $R_2$ represents $C_1$–$C_8$alkoxy, $C_1$–$C_8$alkyl, $C_2$–$C_8$alkenyl, $C_2$–$C_8$alkynyl, $C_3$–$C_{10}$cycloalkyl, heterocycloalkyl, ($C_3$–$C_{10}$cycloalkyl) $C_1$–$C_8$alkyl, heterocycloalkyl) $C_1$–$C_8$alkyl, or 5- or 6-membered aryl or heteroaryl, each of which is unsubstituted or substituted with from 1 to 3 substituents independently selected from $R_5$, where each heterocycloalkyl is a ring having from 3–10 ring members and contains at least one atom selected from N, S, and O, the remaining ring members being carbon atoms;

R3 and R4 are each independently selected from:
(a) hydrogen, halogen, nitro and cyano; and
(b) groups of the formula:

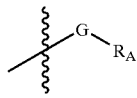

wherein:
(i) G is a bond, $C_1$–$C_8$alkyl, —NH—, —N($R_B$)—, ($R_B$)N— —O—, —C(=O)—, —C(=O)NH—, —C(=O)N$R_B$—, —S(O)$_m$—, —CH$_2$C(=O)—, —S(O)$_m$NH—, —S(O)$_m$N$R_B$—, —NHC(=O)—, —C(=N$R_B$), HC=N—, —N$R_B$C(=O)—, —NHS(O)$_m$— or N$R_B$S(O)—;
(ii) $R_A$ and $R_B$ are independently selected from $C_1$–$C_8$alkyl, $C_2$–$C_8$alkenyl, $C_2$–$C_8$alkynyl and 3- to 12-membered carbocycles and 3- to 12-membered heterocycles,
where each of the carbocycles and heterocycles has 1 ring or 2 fused, pendant or spiro rings,
each heterocycle has at least one ring that comprises at least one heteroatom selected from N, O, and S, the remaining heterocycle members being carbon atoms,
each of the carbocycles and heterocycles is unsubstituted or substituted with from 1 to 4 substituents independently selected from $R_5$; and
(iii) m is 0, 1 or 2; and
$R_5$ is independently selected at each occurrence from halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl)alkyl, ($C_3$–$C_{10}$cycloalkyl)alkoxy, heterocycloalkyl, $C_1$–$C_8$alkenyl, $C_1$–$C_8$alkynyl, halo($C_1$–$C_8$)alkyl, halo($C_1$–$C_8$)alkoxy, oxo, amino($C_1$–$C_8$)alkyl and mono- and di($C_1$–$C_8$alkyl)amino ($C_1$–$C_8$)alkyl, where each heterocycloalkyl is a ring having from 3–10 ring members and at least one atom selected from N, S, and O, and the remaining ring members are carbon atoms.

2. A compound or salt according to claim 1, wherein $R_1$ is a 5- or 6-membered aryl or heteroaryl, unsubstituted or substituted with from 1 to 3 groups independently selected from $R_5$.

3. A compound or salt according to claim 2, wherein $R_1$ is phenyl, pyridyl, pyrimidyl or thiazolyl, unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy.

4. A compound or salt according to claim 3, wherein $R_1$ is pyridyl, pyrimidyl or thiazolyl, unsubstituted or substituted with one or two halogens.

5. A compound or salt according to claim 1, wherein $R_2$ is $C_1$–$C_6$alkyl, $C_1$–$C_6$alkoxy, or a 5- or 6-membered heterocycloalkyl or heteroaryl.

6. A compound or salt according to claim 5, wherein $R_2$ is $C_1$–$C_4$alkoxy or $C_1$–$C_4$alkyl.

7. A compound or salt according to claim 1, wherein $R_3$ and $R_4$ are each independently selected from hydrogen, halogen, $C_1$–$C_6$alkyl, $C_1$–$C_6$alkoxy, halo$C_1$–$C_6$alkyl, and 5- to 7-membered aromatic carbocycles and heterocycles, wherein the carbocycles and heterocycles are unsubstituted or substituted with halogen, trifluoromethyl or methyl.

8. A compound or salt according to claim 7, wherein $R_3$ and $R_4$ are independently hydrogen, halogen, methoxy, ethoxy, methyl or phenyl, wherein the phenyl is unsubstituted or substituted with halogen, trifluoromethyl or methyl.

9. A compound or salt according to claim 1, wherein:
$R_1$ is pyridyl or pyrimidyl, unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy;
$R_2$ is $C_1$–$C_4$alkoxy or $C_1$–$C_4$alkyl; and
$R_3$ and $R_4$ are independently hydrogen, halogen, $C_1$–$C_6$alkoxy or optionally substituted phenyl.

10. A compound according to claim 1, which is 2-[2-(6fluoro-pyridin-2-yl)-imidazol-1-ylmethyl]-3-methoxy-5-phenyl-pyrazine.

11. A compound according to claim 1, which is 3-methoxy-5-phenyl-2-(2-thiazol-2-yl-imidazol-1-ylmethyl)-pyrazine.

12. A compound according to claim 1, which is 2-[2-(6-fluoro-pyridin-2-yl)-imidazol-1-ylmethyl]-3,5-dimethoxy-pyrazine.

13. A compound according to claim 1, which is 2-[2-(6-fluoro-pyridin-2-yl)-imidazol-1-ylmethyl]-3,5-diethoxy-pyridine.

14. A compound according to claim 1, which is 3,5-dimethoxy-2-(2-thiazol-2-yl-imidazol-1-ylmethyl)-5-pyrazine.

15. A compound according to claim 1, which is 2-[2-(6-fluoro-pyridin-2-yl)-imidazol-1-ylmethyl]-5-methoxy-3-pyridin-2-yl-pyrazine.

16. A compound according to claim 1, which is 2-[1-(3,5-methoxy-pyrazin-2-ylmethyl)-1H-imidazol-2-yl]-pyrimidine.

17. A compound according to claim 1, which is 2-[1-(5-methoxy-3-piperidin-1-yl-pyrazin-2-ylmethyl)-1H-imidazol-2-yl]-pyrimidine.

18. A pharmaceutical composition comprising a compound according to claim 1, in combination with a physiologically acceptable carrier or excipient.

19. The pharmaceutical composition of claim 18 wherein the pharmaceutical composition is formulated as an injectable fluid, an aerosol, a cream, a gel, a pill, a capsule, a syrup, or a transdermal patch.

20. A packaged pharmaceutical preparation comprising the pharmaceutical composition of claim 18 in a container and instructions for using the composition to treat a patient suffering from anxiety, depression, a sleep disorder, attention deficit disorder, or Alzheimer's dementia.

* * * * *